United States Patent
Shukla et al.

(10) Patent No.: US 11,931,482 B2
(45) Date of Patent: Mar. 19, 2024

(54) AURANOFIN-RELEASING ANTIBACTERIAL AND ANTIBIOFILM POLYURETHANE INTRAVASCULAR CATHETER COATINGS

(71) Applicants: BROWN UNIVERSITY, Providence, RI (US); Rhode Island Hospital, Providence, RI (US)

(72) Inventors: Anita Shukla, Providence, RI (US); Beth Fuchs, Quincy, MA (US); Hanyang Liu, E. Providence, RI (US); Eleftherios Mylonakis, Providence, RI (US)

(73) Assignees: BROWN UNIVERSITY, Providence, RI (US); Rhode Island Hospital, Providence, RI (US)

(*) Notice: Subject to any disclaimer, the term of this patent is extended or adjusted under 35 U.S.C. 154(b) by 449 days.

(21) Appl. No.: 16/823,163

(22) Filed: Mar. 18, 2020

(65) Prior Publication Data
US 2020/0297898 A1 Sep. 24, 2020

Related U.S. Application Data

(60) Provisional application No. 62/821,209, filed on Mar. 20, 2019, provisional application No. 62/820,120, filed on Mar. 18, 2019.

(51) Int. Cl.
*A61L 29/16* (2006.01)
*A61L 29/08* (2006.01)
(Continued)

(52) U.S. Cl.
CPC ............ *A61L 29/16* (2013.01); *A61L 29/085* (2013.01); *C09D 5/14* (2013.01); *C09D 175/04* (2013.01); *A61L 2300/102* (2013.01)

(58) Field of Classification Search
CPC ........ A61L 27/54; A61L 29/16; A61L 29/085; A61L 2300/102; C09D 5/14; C09D 175/04

See application file for complete search history.

(56) References Cited

U.S. PATENT DOCUMENTS 6,153,252 A   11/2000  Hossainy et al.
6,641,831 B1 * 11/2003  Schierholz .............. A61L 29/16
                                                         424/424

(Continued)

FOREIGN PATENT DOCUMENTS

CN    110694136 A    1/2020
DE    102004046244 A1    3/2006

(Continued)

OTHER PUBLICATIONS

Danese, Paul N., "Antibiofilm Approaches: Prevention of Catheter Colonization", Chemistry & Biology, vol. 9, Aug. 2002, pp. 873-880.

(Continued)

*Primary Examiner* — Dah-Wei D. Yuan
*Assistant Examiner* — Andrew J Bowman
(74) *Attorney, Agent, or Firm* — Adler Pollock & Sheehan P.C.

(57) ABSTRACT

The invention provides an auranofin-releasing antibacterial and antibiofilm polyurethane (PU) catheter coating. Auranofin is an antirheumatic drug with recently identified antimicrobial properties.

20 Claims, 9 Drawing Sheets
(4 of 9 Drawing Sheet(s) Filed in Color)

(51) Int. Cl.
    *C09D 5/14*     (2006.01)
    *C09D 175/04*   (2006.01)

(56) References Cited

U.S. PATENT DOCUMENTS

| | | | |
|---|---|---|---|
| 6,787,179 | B2 | 9/2004 | Timm et al. |
| 7,541,048 | B2 | 6/2009 | Dewitt et al. |
| 7,914,841 | B2 | 3/2011 | Eells et al. |
| 8,414,909 | B2 | 4/2013 | Wang |
| 8,679,520 | B2 | 3/2014 | Horres et al. |
| 8,784,862 | B2 | 7/2014 | Horres et al. |
| 8,916,227 | B2 | 12/2014 | Horres et al. |
| 9,192,697 | B2 | 11/2015 | Hoffmann et al. |
| 10,293,085 | B2 | 5/2019 | Orlowski |
| 2003/0040501 | A1* | 2/2003 | Newman ............ A61M 37/0092 514/44 R |
| 2004/0022853 | A1* | 2/2004 | Ashton .................. A61L 29/16 424/468 |
| 2011/0076319 | A1 | 3/2011 | Orlowski et al. |
| 2011/0150961 | A1 | 6/2011 | Perry et al. |
| 2013/0103139 | A1 | 4/2013 | Hoffmann et al. |
| 2016/0082159 | A1 | 3/2016 | Orlowski |

FOREIGN PATENT DOCUMENTS

| | | |
|---|---|---|
| DE | 102005039126 A1 | 2/2007 |
| EP | 3442612 A1 | 2/2019 |
| WO | 2014/008875 A1 | 1/2014 |
| WO | 2017/053778 A1 | 3/2017 |
| WO | 2018/204782 A1 | 11/2018 |
| WO | 2018/213352 A1 | 11/2018 |

OTHER PUBLICATIONS

Díez-Martínez, et al., "Auranofin-Loaded Nanoparticles as a New Therapeutic Tool to Fight Streptococcal Infections", Scientific Reports, vol. 6, No. 19525, Jan. 18, 2016, pp. 1-12.

Fuchs, et al., "Inhibition of Bacterial and Fungal Pathogens by the Orphaned Drug Auranofin", Future Medicinal Chemistry, vol. 8, Issue 2, 2016, pp. 117-132.

Gabriella, et al., "Efficacy of a Central Venous Catheter (Hydrocath®) Loaded with Teicoplanin in Preventing Subcutaneous Staphylococcal Infection in the Mouse", Zentralblatt Fur Bakteriol, vol. 279, 1993, pp. 426-433.

Harbut, et al., "Auranofin Exerts Broad-spectrum Bactericidal Activities by Targeting Thiol-redox Homeostasis", Proceedings of the National Academy of Sciences, U S A., vol. 112, Issue 14, Apr. 7, 2015, pp. 4453-4458.

Liu, et al., "Auranofin Releasing Antibacterial and Antibiofilm Polyurethane Intravascular Catheter Coatings", Frontier in Cellular and Infection Microbiology, vol. 9, No. 37, Feb. 28, 2019, pp. 1-13.

Maki, et al., "The Risk of Bloodstream Infection in Adults with Different Intravascular Devices: A Systematic Review of 200 Published Prospective Studies", Mayo Clinic Proceedings, vol. 81, No. 9, Sep. 2006, pp. 1159-1171.

Stacey, Kevin, "Germ-Fighting Catheter Coating May Help Prevent Infections", News from Brown Available at <https://news.brown.edu/articles/2019/03/coating>, Mar. 7, 2019, 3 pages.

Zhou, et al., "In Vivo Anti-Biofilm and Anti-Bacterial Non-Leachable Coating Thermally Polymerized on Cylindrical Catheter", ACS Applied Materials and Interfaces, vol. 9, 2017, pp. 36269-36280.

\* cited by examiner

AURANOFIN-RELEASING ANTIBACTERIAL AND ANTIBIOFILM POLYURETHANE INTRAVASCULAR CATHETER COATINGS

REFERENCE TO RELATED APPLICATIONS

This matter claims priority under 35 U.S.C. § 119(e) to U.S. Ser. No. 62/820,120, filed Mar. 18, 2019, and U.S. Ser. No. 62/821,209, filed Mar. 20, 2019.

STATEMENT REGARDING FEDERALLY SPONSORED RESEARCH OR DEVELOPMENT

This invention was made with government support under Grant Nos. AI083214 and GM121344 awarded by the National Institutes of Health (NIH), and Grant No. N00014-17-1-2120 awarded by the Office of Naval Research (ONR). The government has certain rights in the invention.

FIELD OF THE INVENTION

This invention generally relates to materials for grafts or prostheses or coating grafts or prostheses, including a coating for rendering implantable materials antimicrobial or antibiofilm.

BACKGROUND OF THE INVENTION

Catheter-related bloodstream infections (CRBSI) are costly complications of intravascular catheter use. Intravascular catheters are used for hemodynamic monitoring, renal replacement therapy, nutritional support, and administration of medications. Alberti et al., Diabet. Med., 15, 6-12 (2014). Catheter-related bloodstream infections are a leading cause of hospital-acquired infections worldwide, resulting not only in the burden of cost and morbidity for patients but also in the over-consumption of medical resources for hospitals and health care organizations. More than 150 million intravascular catheters are implanted each year in the United States. Shah et al., Neurohospitalist, 3, 144-151 (2013). Infections arising from these implants develop in about 250,000 patients a year in the United States alone. CRBSIs are the most common source of nosocomial bacteremia. See, Grady et al., Clin. Infect. Dis. 49, 1-45 (2014); Maki et al., Mayo Clin., Proc., 81, 1159-71 (2006); Abebe et al., Hosp. Med. Clin., 3, e32-e49 (2014). Those infections are fatal in 12-25% of the patients. Maki et al., Mayo Clin., Proc., 81, 1159-71 (2006). Infections arising from bacterial-colonized catheters prolong hospital stays from ~10 to 20 days and increase the cost of care from $4,000 to $56,000 per patient. Maki et al., Mayo Clin., Proc., 81, 1159-71 (2006).

CRBSIs are mostly caused by Gram-positive bacteria, including species of *Staphylococcus aureus*, the most common type of hospital-acquired infection. Abebe et al., Hosp. Med. Clin., 3, e32-e49 (2014). Intravascular catheters can become infected by microorganisms in several ways. The catheter lumen can be contaminated before use. The skin microbiome can contaminate the catheter tip and cutaneous tract during insertion. Contaminated infusate can deliver bacteria. Inserted materials can be exposed to microbes due to existing systemic infection. Pugach et al., J. Urol., 162, 883-887 (1999); Abebe et al., Hosp. Med. Clin., 3, e32-e49 (2014). After bacteria are in the catheter material, they adhere and begin forming a biofilm, which leads to CRBSI pathogenesis. Donlan, Emerg. Infect. Dis., 8, 881-890 (2002); Raad et al., Antimicrob. Agents Chemother. 51, 1656-1660 (2007).

Previously, but with limited success, catheters have been coated to inhibit bacterial accumulation. Previous antibacterial coatings lost their effectiveness after two weeks at most, often because they release their drug payload too quickly. Previous coatings also have used traditional antibiotics, which raised concerns about antibiotic resistance over long-term use. Available coating reagents are released from the catheter material quickly and do not prolong protection during the full course of implantation. Catheter coatings with long-term antibacterial and anti-biofilm efficacy are not widely reported and not available in clinical practice.

Despite recent progress, developing drug resistance remains a significant concern while utilizing traditional antibiotic therapeutics in catheter technologies. Danese, Chem. Biol. 9, 873-880 2002). There remains a need in the art for an improved method of preventing CRBSIs.

SUMMARY OF THE INVENTION

The invention provides an auranofin-releasing antibacterial and antibiofilm polyurethane (PU) catheter coating. Auranofin (Ridaura®) is an antirheumatic drug with recently identified antimicrobial properties.

In the first embodiment, the invention provides an antibacterial coating. In a second embodiment, the antibacterial coating coats intravascular catheters. This antibacterial coating for intravascular catheters can prevent catheter-related bloodstream infections. The coating kills bacteria and keeps them from forming hard-to-eliminate biofilms. In a third embodiment, the antibiotic is auranofin, which has recently been demonstrated to have a highly potent antibacterial efficacy. The polyurethane drug carrier is a barrier surrounding the antibacterial agent, auranofin, to extend the drug release profile and improve its long-term antibacterial and antibiofilm effectiveness and potentially the length of catheter implantation within a patient. The polyurethane+auranofin (PU+auranofin) coatings are highly stretchable (exhibiting ~500% elongation), which is important for the compliance of the material on a flexible catheter. The polyurethane+auranofin coatings are hemocompatible with human erythrocytes and maintain liver cell viability.

In a fourth embodiment, the invention provides an auranofin-coated medical device. In a fifth embodiment, the device is a polyurethane+auranofin-coated (PU+auranofin-coated) medical device. In a fifth embodiment, the device is an auranofin-coated catheter.

In a sixth embodiment, the invention provides a method for making a polyurethane+auranofin-coated catheter. To make the coating, the researchers dissolved polyurethane and concentrations of auranofin in a solution, which was then deposited onto a catheter. The solvent is then evaporated away, leaving a stretchable yet durable polymer coating. Thus, solvent casting polyurethane+auranofin-coated catheter coatings yielded materials that prevented the attachment of methicillin-resistant *Staphylococcus aureus* (MRSA) and the accumulation of bacteria that enables biofilm formation. Mechanical testing showed that the coating could stretch up to 500% without breaking.

In a seventh embodiment, the invention provides a method for treating catheter-related bloodstream infections, comprising the step of inserting a polyurethane+auranofin-coated catheter into the body of a vertebrate. In an eighth embodiment, the invention provides a method for preventing the growth of methicillin-resistant *Staphylococcus aureus* for an extended time, for example, eight to twenty-six days. Auranofin release profiles estimated in bacteria media demonstrated the potential to achieve twenty-six days of above minimum inhibitory concentration (MIC) release for specific formulations of this coating. A slow, sustained release followed a sizeable initial release on the first day. In early testing, polyurethane+auranofin-coated catheters inhibited the growth of methicillin-resistant *Staphylococcus aureus* for eight to twenty-six days, depending on the specific drug concentration used during the dip-coating process. These coatings exceed the maximal two-week period of efficacy observed for reported antimicrobial catheters.

In a seventh embodiment, the invention provides a method for treating catheter-related bloodstream infections, comprising the step of inserting a polyurethane+auranofin-coated catheter into the body of a vertebrate, wherein it has a catheter-related bloodstream infection, for example, one resulting from the previous insertion of a catheter into the vertebral body.

The polyurethane+auranofin-coated catheters completely inhibited methicillin-resistant *Staphylococcus aureus* (MRSA) biofilm formation in vitro, an effect not observed with auranofin or polyurethane alone, a property unique to the combined polyurethane+auranofin coating and not found with auranofin or polyurethane alone.

The PU+auranofin coating did not hurt catheter structure.

These coatings are non-toxic to healthy hRBCs and HepG2 cells, important for future preclinical and clinical translation of these products. Intravascular catheters are currently used over a 72- to 96-hour time period, but this coating may extend that time to 26 days.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 6 is a set of drawings showing the thickness and mechanical properties of coated catheters.

FIG. 7 is a set of drawings showing the antibiofilm efficacy of coated catheters.

FIG. 8 is a pair of bar graphs showing the cytotoxicity of PU+auranofin coatings.

DETAILED DESCRIPTION OF THE INVENTION

Industrial Applicability

Figure 1:
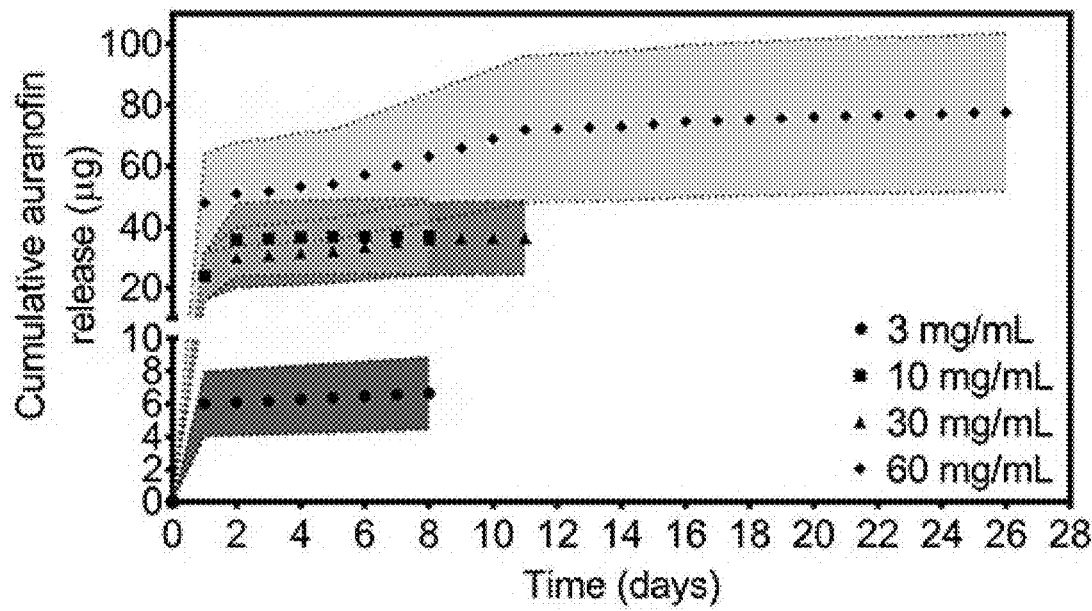
FIG. 1 is a graph showing the in vitro release profile of auranofin in tryptic soy broth glucose (TSBG) medium for PU+auranofin-coated catheters formulated at four auranofin coating concentrations (3 mg/mL, 10 mg/mL, 30 mg/mL, and 60 mg/mL). The inventors evaluated release by examining *Staphylococcus aureus* strain MRSA USA300 bacterial inhibition. The data are shown as a range set by the upper and lower limits of the auranofin minimum inhibitory concentration (MIC) for each day at which the release solution auranofin concentration was above minimum inhibitory concentration for MRSA USA300 (n=3).

This invention usefully provides an improved device, material, and method to prevent microbial colonization of catheters. The inventors wanted to develop a coating that could both kill planktonic (free-floating) bacteria and prevent the colonization of bacteria on surfaces. The invention provides catheter materials coated with auranofin afford extended protection against the major bacterial pathogen *Staphylococcus aureus*.

The invention provides a polyurethane coating that can be readily applied to various medically relevant surfaces and gradually release a drug called auranofin that can kill methicillin-resistant *Staphylococcus aureus* (MRSA) bacteria for nearly a month in laboratory assays. The assays also showed that the coating could prevent the formation of MRSA biofilms, which, once established, are extraordinarily resilient to antimicrobial treatment.

Auranofin (Ridaura®) was initially developed and approved by the U.S. Food and Drug Administration to treat arthritis but is also highly effective in killing methicillin-resistant *Staphylococcus aureus* and other dangerous microbes. Fuchs et al., Future Med. Chem., 8(2), 117-132 (2016). Advantageously, auranofin works in a way that makes it difficult for bacteria to evolve natural drug resistance.

To test the coating's effectiveness, the researchers placed coated catheters in methicillin-resistant *Staphylococcus aureus* (MRSA) both in solution and on agar plates on which MRSA bacteria thrive. The experiments showed that the coatings inhibited MRSA growth for up to twenty-six days, depending on the initial concentration of auranofin used in the coating.

The researchers also used bioluminescence imaging to look for signs of biofilm formation. These images showed that the coatings prevent any trace of biofilm. For comparison, the researchers also tested a catheter loaded with vancomycin, a traditional antibiotic highly effective against free-floating methicillin-resistant *Staphylococcus aureus*, but which cannot prevent biofilm formation. Auranofin-coated samples kept their surroundings clear of bacteria, while uncoated samples did not. Biofilms are known and have been shown to have effective ways of evading antibiotics, which makes them more challenging to treat in terms of the concentration of drug needed compared to planktonic bacteria. That these coatings can prevent biofilms from forming in the first place is medically beneficial.

The inventors' preliminary tests for toxicity showed that the coatings had no adverse effects on human blood or liver cells. The FDA has approved both of the coating's components for other uses, which could speed the approval process for in vivo testing. These results may soon translate to the clinic.

Definitions

For convenience, the meaning of some terms and phrases used in the specification, examples, and appended claims, are provided below. Unless stated otherwise or implicit from context, the following words and phrases have the meanings provided below. These definitions are provided to aid in describing particular embodiments and are not intended to limit the claimed invention. Unless otherwise defined, all technical and scientific terms have the same meaning as commonly understood by one of ordinary skill in the art to which this invention belongs. If there is an apparent discrepancy between the usage of a term in the art and its definition provided in this specification, the definition provided in this specification shall prevail.

"Auranofin" (Ridaura®) is a gold salt classified by the World Health Organization as an antirheumatic agent (IUPAC name: Gold(+1) cation; 3,4,5-triacetyloxy-6-(acetyloxymethyl) oxane-2-thiolate; triethylphosphanium). Auranofin, which has been used in the treatment of rheumatic arthritis, has recently been demonstrated to have a highly potent antibacterial efficacy. Fuchs et al., Future Med. Chem., 8(2), 117-132 (2016); Harbut et al., Proc. Natl. Acad. Sci., USA, 112(14), 4453-8 (2015); Torres et al., Antimicrob. Agents Chemother., 60(10), 5663-5672 (2016). Auranofin is an FDA approved antirheumatic therapeutic that is a promising antimicrobial candidate, having shown antibacterial and antifungal efficacy. Cassetta et al., Biometals, 27, 787-791 (2014); Harbut et al., Proc. Natl. Acad. Sci. U.S.A. 112, 4453-4458 (2015); Fuchs et al., Future Med. Chem., 8(2), 117-132 (2016); Thangamani et al., Int. J. Antimicrob. Agents, 47, 195-201 (2016)) along with potent antibiofilm efficacy (Torres et al., Antimicrob. Agents Chemother., 60(10), 5663-5672 (2016); AbdelKhalek et al., Sci. Rep., 8, 8353 (2018).

"Biofilms" are surface-attached, three-dimensional microbial colonies, consisting of bacteria embedded within a self-secreted matrix containing proteins, polysaccharides, and extracellular DNA. Donlan, Emerg. Infect. Dis., 8, 881-890 (2002). After biofilms develop on medical device surfaces, they can lead to device failure. Danese, Chem. Biol. 9, 873-880 2002). Biofilms may also spread infection by releasing planktonic cells, which can colonize downstream sites. Costerton, Science, 284, 1318-1322 (1999); Stewart, Int. J. Med. Microbiol., 292, 107-113 (2002); Lewis et al., in Biofilms, Infection, and Antimicrobial Therapy (Boca Raton, FL, USA: Taylor & Francis, 2005), pp. 241-256.). Eradication of biofilms is a formidable challenge due to the many sophisticated mechanisms bacteria develop to protect against host defense mechanisms and the prevalence of increased resistance against traditional antibiotic treatments. Stewart, Int. J. Med. Microbiol., 292, 107-113 (2002); Flemming et al., Nat. Rev. Microbiol., 14, 563-575 (2016); Koo et al., Nat. Rev. Microbiol., 15, 740-755 (2017). The biofilm matrix forms a physical barrier hindering penetration and diffusion of antimicrobial agents. Costerton, Science, 284, 1318-1322 (1999); Stewart, Int. J. Med. Microbiol., 292, 107-113 (2002)), while the low metabolic state of biofilm bacteria make them less susceptible to antibiotics. Brown & Rowland, J. Antimicrob. Chemother., 22, 777-780 (1988); de la Fuente-Núñez et al., Curr. Opin. Microbiol., 16, 580-589 (2013). Additionally, bacteria also coordinate their physiological processes through quorum sensing, allowing the cells to communicate by releasing and responding to small molecules aiding in colonization, defense against antimicrobials, and adaptation to the microenvironment. Li & Tian, Stress Environ. Regul. Gene Expr. Adapt. Bact., 2, 1197-1205 (2016); Donlan, Emerg. Infect. Dis., 8, 881-890 (2002). The accumulation of biofilm within the catheter can lead to the need for implant removal.

"Catheters" has the U.S. National Cancer Institute's definition (provided at the NCI Dictionary of Cancer Terms website) of a device used to draw blood and give treatments, including intravenous fluids, drugs, or blood transfusions. A thin, flexible tube is inserted into a vein. It is guided (threaded) into a large vein. An access catheter can stay in place for weeks or months and helps avoid the need for repeated needle sticks.

"Catheter-related bloodstream infections (CRBSIs)" are defined as the presence of bacteremia originating from an intravenous catheter. Gahalot et al., Int. J. Crit. IIIn. Inj. Sci., 4(2): 162-167 (April-June 2014).

"Coating" has the plain meaning of a thin layer or covering of something or material used for making coats. See, New Oxford American Dictionary, third edition, (August 2010).

"Cover" has the plain meaning of extending over (e.g., a surface) or enveloping a layer of something. See, New Oxford American Dictionary, third edition, (August 2010). A cover usually, but not necessarily, closes the object.

"Methicillin-resistant *Staphylococcus aureus* (MRSA)" refers to a group of Gram-positive bacteria genetically distinct from other strains of *Staphylococcus aureus*. MRSA is any strain of *S. aureus* that has developed, through horizontal gene transfer and natural selection, multiple drug resistance to beta-lactam antibiotics. *Staphylococcus aureus* strain MRSA USA300 is a community-associated MRSA strain. *Staphylococcus aureus* strain MRSA USA300 engineered to express luciferase (USA300 Lac::Lux) was supplied by Dr. Michael Hamblin at Massachusetts General Hospital (Boston, MA, USA). Dai et al., Photomed. Laser Surg., 31, 531-538 (2013).

"Vertebrate" has the widely known and understood meaning of an animal with a segmented bony or cartilaginous spinal cord. "Mammal" has the widely known and understood meaning of vertebrates that suckle their young. "Human" has the plain meaning of a human being, *Homo sapiens*. When used as an adjective, "human" has the plain meaning of relating to or characteristic of people or human beings. See, New Oxford American Dictionary, third edition, (August 2010). Humans are a subset of mammals, and mammals are a subset of vertebrates.

Composition of Matter

This invention provides a coating that incorporates auranofin; an FDA approved antirheumatic therapeutic with recently identified antimicrobial activity. Auranofin exhibits effective antimicrobial activity primarily against Gram-positive pathogenic bacteria, including *Mycobacterium tuberculosis, Bacillus subtilis*, and *Enterococcus faecalis*, drug-sensitive and drug-resistant *Enterococcus faecium*, and *Staphylococcus aureus*. Harbut et al., Proc. Natl. Acad. Sci. U.S.A. 112, 4453-4458 (2015). The minimum inhibitory concentration (MIC) of auranofin against these bacteria is as low as 0.25 µg/mL. Hassanein et al., Future Med. Chem., 9, 553-578 (2017).

Auranofin has a unique mechanism of action that relies on its potent inhibition of bacterial thioredoxin reductase, an important protein in thiol based redox metabolism essential in maintaining cellular processes including protection against reactive oxygen species, protein folding, and DNA synthesis. Lundstrom & Holmgren, J. Biol. Chem., 265, 9114-9120 (1990); Ritz & Beckwith, Annu. Rev. Microbiol. 55, 21-48 (2001); Lu & Holmgren, Free Radic. Biol. Med., 66, 75-87 (2014). Inhibiting the bacterial thioredoxin reductase and disrupting the redox balance results in bacterial cell death. Bonilla et al., J. Biol. Chem., 283, 17898-17907 (2008); Debnath et al., Nat. Med., 18, 956-960 (2012); Tejman-Yarden et al., Antimicrob. Agents Chemother., 57, 2029-2035 (2013). This antibacterial drug target is limited for developing drug resistance, unlike the drug targets for previously used antibiotics. Lin et al., PLoS Pathog., 12, e1005675 (2016); Sweeney et al., Antibiotics, 6, E4 (2017).

Characterization of Coating Morphological and Mechanical Properties.

The thicknesses of PU+auranofin and polyurethane only coatings on PTFE were evaluated using a Dektak3 profilometer (Bruker, Santa Barbara, CA, USA). The average step height was measured at three random locations on the coated material. Tensile testing of the standalone films was carried out using an Instron Series 5942 Universal Testing System (Norwood, MA) equipped with a 500 N load cell. An extension rate of 0.1 mm/s was employed until material failure was noted. The pre-yield elastic deformation region (up to 15% extension) of the engineering stress vs. strain curve was used to determine the tensile elastic modulus of the film. The interior and outer coating surfaces on the coated catheters, along with non-coated catheters, were imaged using an LEO Gemini 1530 scanning electron microscope (SEM, Carl Zeiss, Oberkochen, Germany). Before SEM imaging, the catheters were sputter-coated with gold and palladium. Coated and non-coated catheters were also imaged using an inverted tissue culture trinocular microscope (AmScope, Irvine, CA, USA) equipped with an AmScope MU500 eyepiece camera (5.1 MP Aptina Color CMOS) and 4× objective lens.

Statistical Analysis.

All analyses were conducted in triplicate at a minimum. All data are reported as mean±standard deviation. Statistical significance was calculated using GraphPad Prism with either a two-tailed t-test or one- or two-way analysis of variance (ANOVA) with Tukey's posthoc analysis, as appropriate. Data were considered statistically significant for $p<0.05$.

Device

Taking advantage of the recently discovered antimicrobial properties of auranofin, the inventors have developed a polyurethane (PU) coating embedded with auranofin that can be used to coat medical devices, including intravascular catheters. The polyurethane controls auranofin release from the material.

The auranofin-coated catheter material is resistant to bacterial collection and biofilm accumulation, thus preserving the life of the catheter after it is inserted into patients. These coatings are non-toxic to healthy hRBCs and HepG2 cells, important for future preclinical and clinical translation of these products. Intravascular catheters can be used over a 72- to 96-hour time period. Brown & Rowland, J. Fam. Pract., 62, 200-202 (1988). Adding an inhibitory drug such as auranofin in the form of a sustained-release coating can prevent infection by planktonic and biofilm bacteria, potentially limiting CRBSIs and extend catheter use significantly.

Catheter Coating Morphology and Mechanical Properties.

Figure 5:
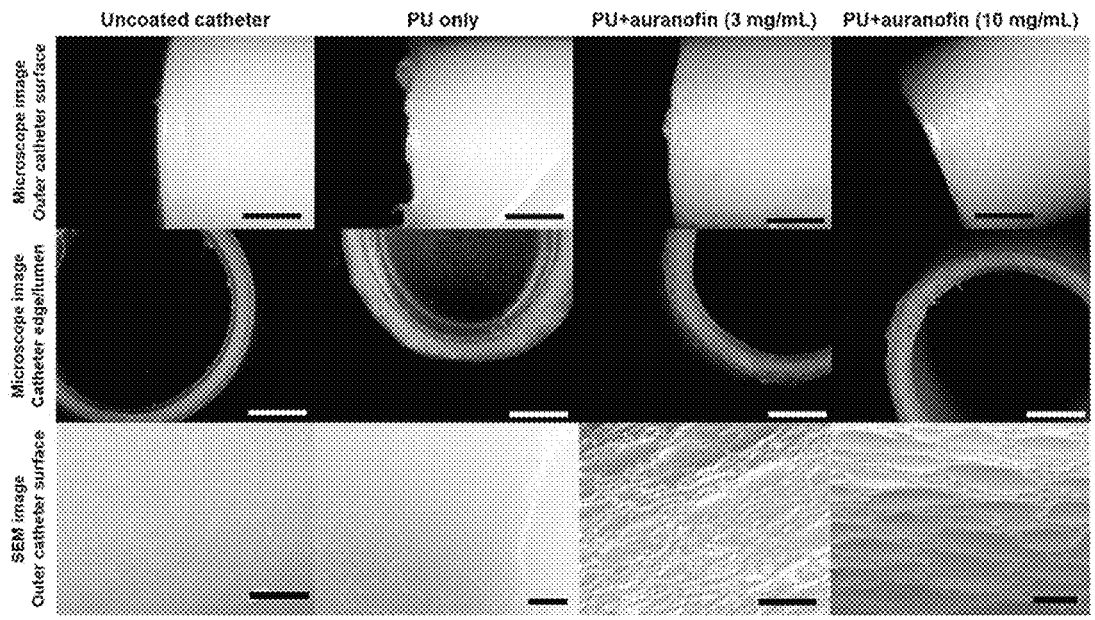
FIG. 5 is a set of photographs showing catheter coating morphology examined via light microscopy and scanning electron microscopy (SEM). Coatings formulated with polyurethane only and PU+auranofin at auranofin concentrations of three and ten mg/mL coated for one day are shown. Scale bars=500 μm (light microscope) and 50 μm (scanning electron microscopy).

Having determined that PU+auranofin coatings lead to effective auranofin release and methicillin-resistant *Staphylococcus aureus* inhibition, the inventors sought to determine if coating the catheter altered the implant material. Light microscope images of the coatings formulated with PU+auranofin solutions containing three and ten mg/mL auranofin demonstrate a slightly rough exterior, with discernible differences from the polyurethane only coated Teflon catheter (FIG. 5). SEM imaging of the catheters confirmed surface texturization in the PU+auranofin-coated catheters compared to the polyurethane only coated catheters (FIG. 5). Compared with polyurethane only coatings, the added surface texture may result from the interaction of auranofin with the polyurethane during the drying process, preventing a completely smooth surface from forming.

Figure 6A:
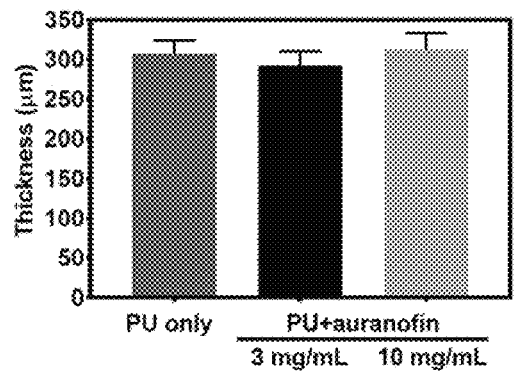
FIG. 6(A) is a bar graph showing the thickness of polyurethane only and PU+auranofin (three mg/mL and ten mg/mL auranofin coating concentration) on PTFE.

The thickness of these coatings on flat PTFE sheets was examined via profilometry for PU+auranofin coatings formulated with auranofin coating concentrations of three and ten mg/mL. FIG. 6A shows the average thickness of PU only and PU+auranofin coatings. The average thickness of polyurethane only coatings was 307.7±16.6 μm; auranofin-loaded polyurethane coatings had average thicknesses of 292.5±17.7 and 313.1±20.5 μm for three and ten mg/mL auranofin, respectively. The presence of auranofin did not lead to statistically significant changes in coating thicknesses between these three groups, despite the effect on coating morphology.

Figure 6B:
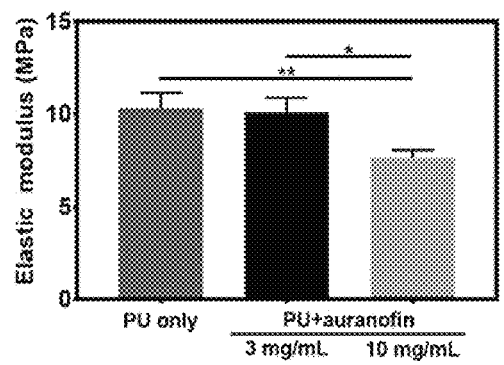
FIG. 6(B) is a bar graph showing the tensile elastic moduli of polyurethane and PU+auranofin (three mg/mL and ten mg/mL auranofin coating concentration) standalone coatings. Scale bars=25-mm.
Figure 6C:
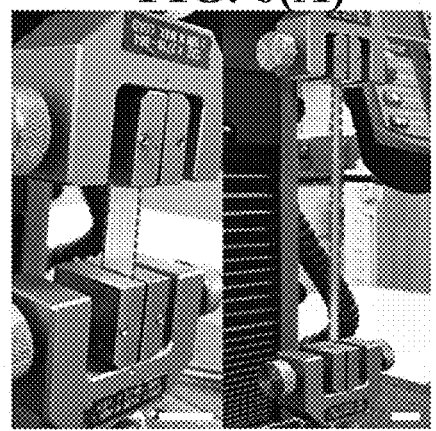
FIG. 6(C) is a representative digital image displaying elongation of standalone PU+auranofin coating formulated with three mg/mL auranofin during tensile testing nearing failure.
Figure 6D:
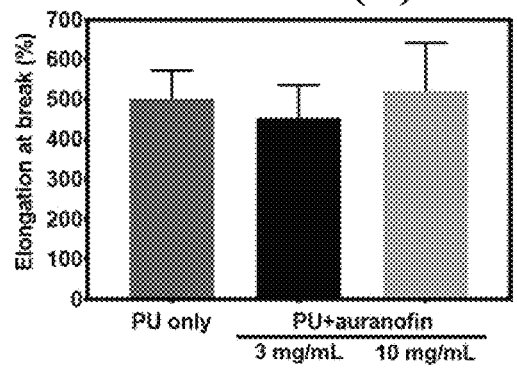
FIG. 6(D) is a bar graph showing the percent elongation at break of polyurethane and PU+auranofin (three mg/mL and ten mg/mL auranofin coating concentration) standalone coatings. Data are shown as mean±standard deviation with *$p<0.05$ and **$p<0.001$ for moduli values between samples analyzed using one-way ANOVA with Tukey's posthoc analysis (n=3).

To further evaluate the mechanical properties of the PU+auranofin coatings, tensile tests were performed on standalone coatings. As seen in FIG. 6B, polyurethane coating stiffness decreased when ten mg/mL, but not three mg/mL auranofin was included in the coating process compared to polyurethane only. Polyurethane only coatings exhibited an elastic modulus of 10.3±0.8 MPa vs. 10.1±0.8 MPa and 7.7±0.4 MPa for PU+auranofin coatings formulated from three to ten mg/mL auranofin, respectively. The decreased stiffness may result from disruption of the hydrogen bonding in the polyurethane hard segments, which is known to reinforce the material. Shoeib et al., Inorganica Chim. Acta 363, 184-192 (2010). This effect has been observed with poly(ethylene glycol), where the oxygen atoms in the backbone act as hydrogen bond acceptors that weaken the hard polyurethane segments. Park et al., J. Biomater. Sci. Polym. Ed. 12, 629-645 (2001). The auranofin molecule has nine hydrogen bond acceptors and may have a similar effect. The coatings are highly stretchable, as seen in FIG. 6C. There was no statistical difference between the percent elongation at break (~500%) between polyurethane coatings formulated with and without auranofin (FIG. 6D), in agreement with what has previously been reported for polyurethane coatings. La Francesca et al., Sci. Rep., 8, 4123 (2018). Overall, the incorporation of auranofin does not appreciably impact the tensile properties of these coatings compared to polyurethane only, maintaining a high degree of stretchability, which will be important for future clinical use on catheters.

Figure 13:
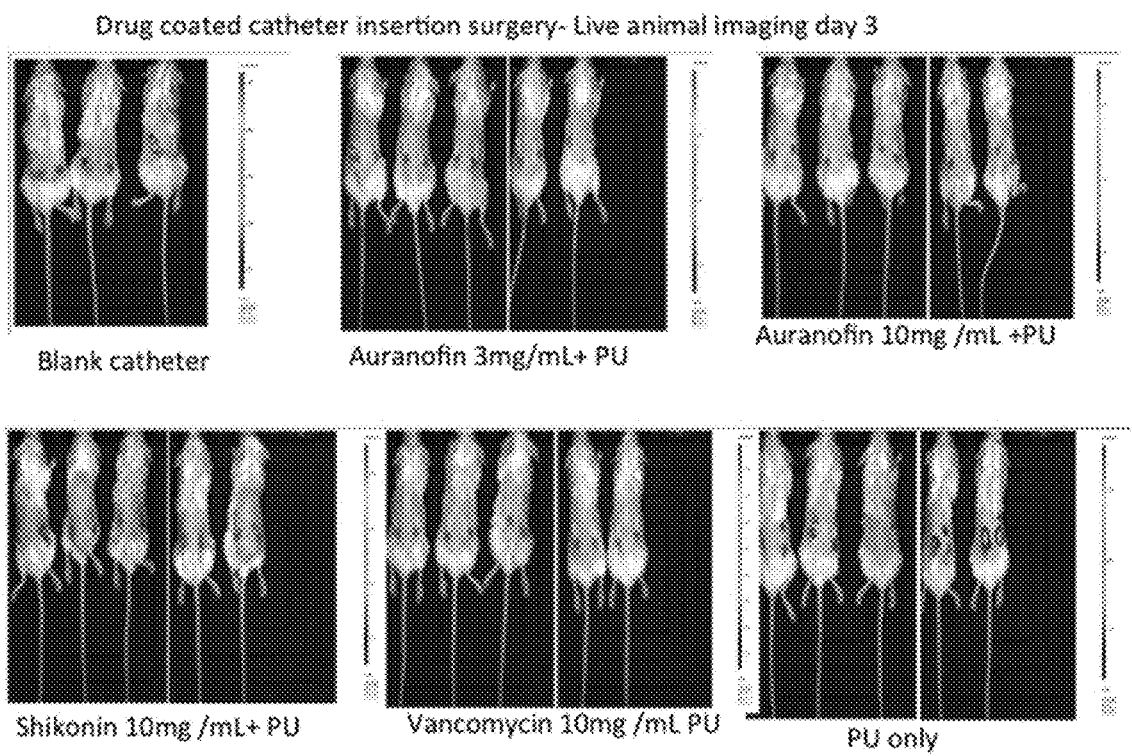
FIG. 13 visualizes *Staphylococcus aureus* USA300 drug-coated catheters implanted into the hind flanks of mice. A luminescent USA300 strain is used to observe bacteria associated with the subcutaneously implanted catheters. Uncoated catheters (blank) exposed to *S. aureus* cells are compared to catheters coated with 3 mg/mL auranofin and PU, 10 mg/mL auranofin, and PU, 10 mg/mL shikonin and PU, 10 mg/mL vancomycin and PU, and PU alone.
Figure 14:
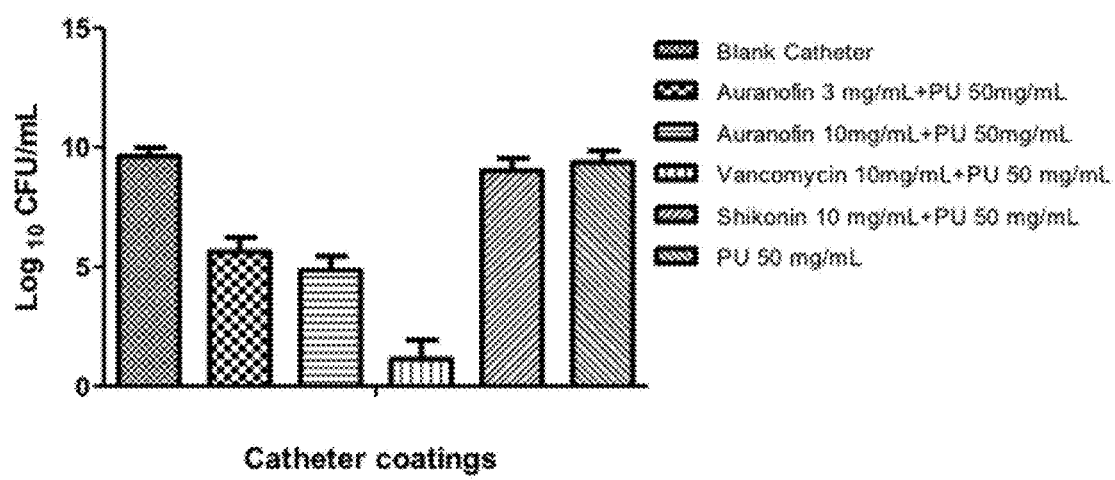
FIG. 14 shows removed subcutaneous catheters removed, submerged in PBS, and subjected to sonication to release the attached *S. aureus* for enumeration on solid media plates. Colony-forming units were counted and compared for catheters removed four days after subcutaneous implantation. Uncoated catheters (blank) exposed to *S. aureus* cells are compared to catheters coated with 3 mg/mL auranofin and PU, 10 mg/mL auranofin, and PU, 10 mg/mL shikonin and PU, 10 mg/mL vancomycin and PU, and PU alone.

Auranofin coating was visualized by IVIS and observed to prevent *S. aureus* accumulation on catheters compared to uncoated catheter material where *S. aureus* attached to catheter surfaces (FIG. 7). The coated catheters initially dipped in *S. aureus* cultures were implanted subcutaneously in mouse flanks and observed with IVIS. After four days, animals were imaged to observed *S. aureus* accumulation at the catheter implant site. Auranofin-coated and vancomycin-coated catheters were observed to have lower *S. aureus* at the implant sites (FIG. 13). The subcutaneous catheters were removed from mice, submerged in phosphate-buffered saline, and subjected to sonication to detach *S. aureus* from the catheter surfaces. The solution was then plated on bacteria growth media overnight at the colony-forming units enumerate to determine the amount of *S. aureus* attached to the catheter. Catheters coated in 10 mg/mL vancomycin had the fewest number of bacteria cells, followed by catheters coated with 10 mg/mL auranofin (FIG. 14).

Materials for Use in Making Polyurethane Coatings

Aromatic polyether-based polyurethane (Texin RxT85A) was supplied by Covestro AG (Leverkusen, Germany).

The antibacterial drug, auranofin, was purchased from Santa Cruz Biotechnology (Dallas, TX, USA).

All solvents, chemicals, and media, unless otherwise noted, were purchased from MilliporeSigma (St. Louis, MO, USA).

Bacto agar was obtained from BD Biosciences (San Jose, CA). Ultrapure deionized water (18.2 MΩ·cm, Milli-Q, EMD Millipore, Taunton, MA) was used in all experiments. Surflo fourteen-gauge Teflon intravenous catheters [2.15 O.D. (1.73 I.D.)×51-mm] were supplied by Patterson Veterinary (Devens, MA, USA).

Polytetrafluoroethylene (PTFE) sheets (AMS 3651) measuring 30 cm by 30 cm with a thickness of 0.38-mm, were obtained from Amazon (Seattle, WA, USA).

Tryptic soy broth (Remel), Dulbecco's modified Eagle's medium (DMEM, Gibco), fetal bovine serum (FBS, Gibco), and precleaned microscope glass slides were purchased from ThermoFisher Scientific (Waltham, MA, USA).

For cytotoxicity testing, human red blood cells (hRBCs) were obtained from Rockland Immunochemicals (Limerick, PA, USA).

For cytotoxicity testing, human hepatoma cells (ATCC HB-8065 HepG2) were obtained from Dr. Bryan Fuchs at Massachusetts General Hospital (Boston, MA, USA).

Cell proliferation reagent, WST-1, was obtained from Roche (Mannheim, Germany).

Method of Manufacture

The coating process uses a dip-coating approach to attach the PU+auranofin coating on the intravascular catheters to have long-term antibacterial and anti-biofilm efficacy (up to 25+ days of effective release for both antibacterial and anti-biofilm activity against methicillin-resistant *Staphylococcus aureus*).

The coating process entails adding 500 mg of polyurethane (PU) to ten ml of tetrahydrofuran (THF) solvent with shaking overnight to achieve a homogenous solution. Three mg of auranofin was added in PU+THF. The solution was vortexed vigorously to obtain a homogenous auranofin solution. PU+auranofin coatings were developed on intravenous catheters by using a dip-coating approach, Catheters were dipped in the auranofin solution for twenty-four hours and air-dried for five hours, The antimicrobial efficacy of the PU+auranofin coating was independent upon the coating time. FIG. 1 shows that catheters coated in auranofin for one day and seven days were able to inhibit bacteria growth until day 8. Catheters coated for five seconds and for one hour exhibited antibacterial activity against *Staphylococcus aureus* for seven days. The release was only extended for one additional day when the coating was prolonged for an extra twenty-three hours/day. Thus, allowing the catheter material to incubate with the PU+auranofin solution beyond one day did not impressively increase the release time. Therefore, in terms of production, coating for short periods of one hour or less is feasible production methods for generating inhibitory conditions.

Polyurethane Coatings.

Auranofin-containing polyurethane coatings were developed by first dissolving polyurethane in tetrahydrofuran (THF) at a concentration of 50 mg/mL at 20° C. for twenty-four hours. Auranofin was then added to the polyurethane solution and thoroughly mixed. This PU+auranofin mixture was then used to produce films for (1) thickness measurement, (2) tensile testing, or (3) catheter coating for drug release and in vitro efficacy and cytocompatibility testing. For thickness measurements, flat PTFE substrates measuring 16-mm by 16-mm by 0.38-mm were coated via drop-casting one mL of the PU+auranofin mixture with 0, 3, or ten mg/mL auranofin; coatings were dried at 20° C. until complete THF evaporation was noted, resulting in a dry PU+auranofin coating. For tensile testing, standalone PU+auranofin films were developed similarly to the coatings on PTFE, but instead, two mL of the PU+auranofin mixture was drop cast onto glass slides measuring 25-mm by 75-mm. These coatings were readily peeled off of the glass and cut into rectangles measuring 12-mm by 38-mm for subsequent testing. For the catheter coatings, catheter segments measuring 10-mm in length were dipped into the PU+auranofin solution (one catheter segment per one mL of PU+auranofin mixture) at auranofin concentrations of 0 mg/mL, 3 mg/mL, 10 mg/mL, 30 mg/mL, or 60 mg/mL for twenty-four hours at 20° C. The catheters were removed from this mixture. The solvent in the coatings was allowed to evaporate at 20° C. for twenty-four hours. All coatings were stored at 4° C. before use. Films with no auranofin were denoted "PU only" coatings.

Assessing Auranofin Release.

Figure 3:
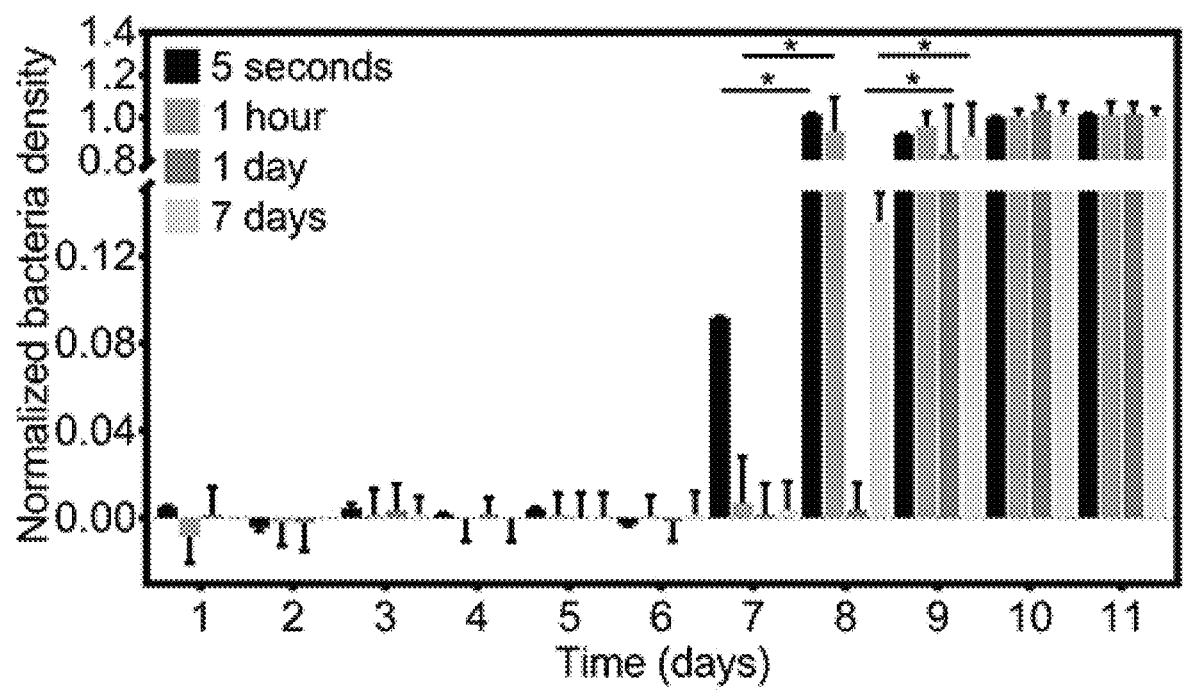
FIG. 3 is a bar graph showing the antibacterial efficacy of PU+auranofin-coated catheters formulated by varying coating times. PU+auranofin coatings were formulated at four coating times (five seconds, one hour, one day, and seven days) at an auranofin coating concentration of three mg/mL. Then, PU+auranofin-coated catheters were incubated with $2\times10^6$ CFU/mL *Staphylococcus aureus* strain MRSA USA300 bacteria. The bars show the normalized bacteria density in tryptic soy broth with glucose (TSBG) medium from catheter groups for timed coating durations against *Staphylococcus aureus* strain MRSA USA300. Normalized bacteria density was determined following eighteen hours. The data are shown as mean±standard deviation where *$p<0.05$ indicates significance between days using two-way ANOVA with Tukey's posthoc analysis (n=3).

To evaluate the auranofin release, the inventors used a Kirby Bauer assay to visualize the bacterial inhibition and determine if the catheter released the auranofin into the surrounding media. Coated catheters were split through the circumference of the material to expose both the inner and outer surfaces. The PU+auranofin-coated catheter exhibited antibacterial efficacy when examining the exposure of the catheter inner and outer sides with various concentrations of auranofin coating solutions. The inventors then placed these catheter pieces were then placed on a bacteria-seeded agar plate with the respective surfaces face down. Inner and outer sides of non-drug-coated catheters on agar plates lacked a zone of inhibition, so the polytetrafluoroethylene (PTFE)-catheter material did not have antibacterial activity against *Staphylococcus aureus*, All of the PU+auranofin-coated catheter groups showed clear inhibition zones when either the outer or inner portion of the catheter was exposed to the bacterial plate. Each group had similar efficacy on inner and outer catheter sides. Coated catheter group in FIG. 2B, FIG. 2C and FIG. 2D indicated similar antibacterial activity, with a more pronounced inhibition zone than the positive control of vancomycin disk (average inhibition diameter 1.48±0.2 cm). In contrast, the coated catheter group treated with three mg/ml of auranofin coating solution exhibited less antibacterial activity compared with other coated concentrations. However, it still had a similar antibacterial activity with positive control. Thus, the coating process appears to apply the releasable drug to both the inner and outer surfaces of the catheters in a dosage-dependent manner,

*Staphylococcus aureus* strain MRSA USA300 biofilm accumulation on catheter segments was determined using IVIS. FIG. 3 shows detecting the bacterial luminescence associated with the catheters. No bioluminescence was shown on PU+auranofin-coated catheters when exposed to three mg/ml or ten mg/ml of auranofin coating solution concentrations. However, PU+vancomycin-coated catheter with the same drug coating concentrations (three mg/ml and ten mg/ml) exhibited the bioluminescent activity of the strain USA300. Even though vancomycin has high antibacterial efficacy against *Staphylococcus aureus*, the drug demonstrated a less effective biofilm inhibition. In FIG. 3, the group of catheters coated with polyurethane alone also showed some anti-biofilm activity in preventing bacterial attachment. This result may be due to the property of the smooth surface of polyurethane, which may inhibit bacterial attachment to the coating surface. Martinez-Martinez et al., J. Hosp. Infect. 16 311-8 (1990); Lopez-Lopez et al., J. Med. Microbiol. 34 349-53 (1991); Zdrahala, J. Biomater. Appl. 1467-EOA (1999). The addition of auranofin enhanced this result.

The colony-forming units (CFU) were determined for each bacteria exposed catheter by sonicating the devices and releasing the bacteria for plating. The collected data confirmed the finding observed through IVIS. There was no bacteria growth on PU+auranofin-coated catheters, but bacteria existed within the biofilm in vancomycin-coated catheter groups. The result of biofilm quantification and bioluminescence imaging confirms that the PU+auranofin-coated catheters have higher anti-biofilm efficacy against *Staphylococcus aureus* as compared to PU+vancomycin-coated catheters.

Method of Preventing and Method of Treatment

Localized delivery can provide rapid antimicrobial activity, minimize offsite toxicity, and lower susceptibility to resistance. Brooks & Brooks, Adv. Drug Deliv. Rev., 78, 14-27 (2014). Auranofin has previously been incorporated into polymeric particles for the localized treatment of bacterial infections. Pearson et al., Macromolecules, 48, 1065-1076 (2015); Diez-Martinez et al., Sci. Rep. 6:19525 (2016).

The inventors report the development and in vitro characterization of an auranofin containing polyurethane (PU) catheter coating that may have the potential to lower the incidence of CRBSIs. The inventors report an auranofin-containing device coating. Polyurethane is an FDA-approved polymer that has been used extensively in biomedical devices for over forty-five years due to its biocompatibility, mechanical flexibility (Ding et al., Soft Matter, 8, 5414-5428 (2012); He et al., J. Appl. Polym. Sci., 126, E354-E361 (2012)), and low protein fouling properties (Xue & Greisler, J. Vasc. Surg. 37, 472-480 (2003); Wilson, Vascular Access: Principles and Practice, 4th edition (Philadelphia, PA: Mosby. 2004); Maki et al., Mayo Clin., Proc., 81, 1159-71 (2006)). Specifically, the inventors used a commercially available aromatic polyether-based polyurethane, Texin RxT85A, to develop the auranofin encapsulating coatings reported in this work. Texin RxT85A has been used in a wide range of medical products, including anesthetic connectors, flexible tubing and films, and catheters. It has also been used to fabricate drug delivery materials, including nanocomposite films and nanofibers that can encapsulate and control the release of antiseptic drugs. Saha et al., J. Appl. Polym. Sci., 131, 1-9 (2014). Here, the inventors demonstrate the sustained release capabilities of auranofin containing polyurethane catheter coatings, which causes the antibacterial and antibiofilm efficacy against methicillin-resistant *Staphylococcus aureus*.

Improvement

Previous methods of preventing microbial colonization of catheters used antimicrobial-loaded or antimicrobial-coated catheters. Antimicrobial agents such as cefazolin (Kamal et al., JAMA J. Am. Med. Assoc. 265, 2364-2368 (1991)), minocycline, rifampin (Raad et al., J. Infect. Dis. 173, 418-424 (1996)), chlorhexidine, and silver sulfadiazine (Maki et al., Ann. Intern. Med., 127, 257-266 (1997)) have been deposited directly on catheter surfaces using dip coating or solvent casting methods. Darouiche et al., N. Engl. J. Med., 340, 1-8 (1999). These coating strategies often lead to the rapid release of the entire antimicrobial payload. Danese, Chem. Biol. 9, 873-880 2002). To provide sustained drug release and long-term therapeutic efficacy, antimicrobials have been incorporated on catheters within polymeric surface coatings. Pugach developed a gelatin hydrogel coating encapsulating ciprofloxacin liposomes on silicone Foley catheters, which significantly delayed bacteria colonization in vivo compared to uncoated catheters. Pugach et al., J. Urol. 162, 883-887 (1999). Fischer coated polyurethane catheters with silver nanoparticles embedded in star-shaped poly(ethylene glycol)-heparin hydrogels, achieving catheter hemocompatibility and antimicrobial functionality for up to a week in vitro. Fischer et al., Biomaterials, 56, 198-205 (2015). Hook identified a group of polymers capable of reducing bacterial attachment up to 30-fold when compared to a commercial silver hydrogel and successfully coated catheters with these polymers demonstrating in vivo antibacterial efficacy. Hook et al., Nat. Biotechnol., 30, 868-875 (2012). Both Fu and Curtin loaded bacteriophage into Lubri-Sil®, a neutral hydrogel coating, on silicone French Foley catheters. Fu et al., Antimicrob. Agents Chemother., 54, 397-404 (2010); Curtin & Donlan, Antimicrob. Agents Chemother. 50, 1268-1275 (2006). Both Fu and Curtin observed a significant reduction in viable biofilm formation by *Staphylococcus epidermidis* on the catheters over twenty-four hours in vitro exposure period. Unfortunately, the antimicrobial efficacy of these previously reported catheter coatings has been limited to a maximum of two weeks.

The following EXAMPLES are provided to illustrate the invention and should not be considered to limit its scope.

Example 1

Quantifying Auranofin Release In Vitro

Auranofin release from PU+auranofin-coated catheters was monitored by incubating each coated catheter in 1.98 mL of tryptic soy broth supplemented with 0.25% glucose (TSBG) at 37° C. with shaking at 110 rpm. Glucose supplementation of tryptic soy broth has previously been shown to promote biofilm formation. Heilmann et al., Infect. Immun., 64, 277-82 (1996); Lim et al., J. Bacteriol., 186, 722-729 (2004). Every twenty-four hours, the release solutions were collected and completely replaced with fresh medium. A microdilution assay, as described by Shukla & Shukla, J. Mater. Chem. B, 6, 6444-6458 (2018), was used to determine the amount of auranofin contained in the media release samples by comparing the antibacterial activity to that of known concentrations of non-coating incorporated auranofin. Briefly, 150 μL of each TSBG release sample was transferred to 96-well plates in triplicate and serially diluted 1:1 (v/v) with tryptic soy broth glucose (TSBG). Controls of non-coating incorporated auranofin were treated similarly. *Staphylococcus aureus* strain MRSA USA300 (10 μL) at a final concentration of 105 CFU/mL in the exponential growth phase (as determined by optical density) was added to these wells. Negative controls of media with no bacteria and positive controls of TSBG with MRSA USA300 in the absence of drug were included. Plates were incubated at 37° C. with shaking at 110 rpm for ~18 hours. Subsequently, the optical density (OD) of the samples was read at 600-nm using a Cytation3 microplate reader (BioTek, Winooski, VT, USA). The normalized bacteria density was calculated using Equation (1).

$$\text{Normalized bacteria density} = \frac{\text{sample } OD - \text{negative control } OD}{\text{positive control } OD - \text{negative control } OD} \quad (1)$$

The minimum inhibitory concentration of the auranofin control against USA300 was determined as the concentration range of auranofin needed to observe a statistically significant transition of normalized bacteria density from zero to greater than zero. The amount of auranofin in the polyurethane coating release media was then estimated by determining how many dilutions of the release media were required to reach this minimum inhibitory concentration transition point and computing a high and low estimate for the concentration of auranofin in the release solution (set by the minimum inhibitory concentration range of non-coating incorporated auranofin).

Auranofin release was also monitored in water (pH 6) at 37° C. for PU+auranofin-coated catheters formulated with auranofin at three and ten mg/mL. These coated catheters were incubated in one mL of water at 37° C. with shaking at 110 rpm. Every twenty-four hours, the release solutions were collected and completely replaced with fresh water. Auranofin in the water release samples was quantified using inductively coupled plasma optical emission spectroscopy (ICP-OES, ThermoFisher, Waltham, MA). ICP-OES can detect the presence of the gold (Au) atom in the auranofin molecule. Briefly, the release samples were diluted 1:4 (v/v) with water for a total sample volume of five mL. This sample was injected into the ICP-OES with a radial plasma view configuration for concentrations above one ppm of auranofin and with an axial plasma view configuration for concentrations below one ppm. The concentration of auranofin in the release solutions was calculated by comparing the intensity of the signal obtained at the characteristic wavelength range of gold (Au) (242.79-242.80 nm) against that of a known auranofin standard examined concurrently.

Example 2

Assessing Coating Antibacterial and Antibiofilm Efficacy In Vitro

Antibacterial and antibiofilm activity of PU+auranofin catheter coatings was examined against MRSA USA300, a community-associated MRSA strain. Kirby-Bauer and broth bacteria survival assays on the coated catheters and their release solutions were conducted, respectively. For the Kirby-Bauer assay, MRSA USA300 in the exponential growth phase at a concentration of 108 CFU/mL was spread on tryptic soy agar plates. PU+auranofin-coated and PU+auranofin-uncoated catheters were cut in half lengthwise using a scalpel. Both the inner and outer surfaces of the catheters were placed in direct contact with the bacteria seeded agar and incubated for twenty-four hours at 37° C. These plates were then photographed using a Canon PowerShot S110 digital camera (Tokyo, Japan).

Long-term antibacterial activity of the coated catheters was confirmed using the MRSA microdilution assays described above. The efficacy of these coatings against a more significant MRSA challenge than a standard microdilution assay ($2\times10^6$ CFU/mL vs. 105 CFU/mL, respectively) was investigated. Coated catheters were incubated in 1.98 mL of tryptic soy broth glucose (TBSG)medium with shaking at 110 rpm at 37° C. The release medium was collected every twenty-four hours and replaced with fresh TSBG medium. A twenty µL suspension of USA300 was added to the release solution to obtain a final bacteria concentration of $2\times10^6$ CFU/mL. This bacterial suspension was incubated with shaking at 110 rpm at 37° C. for twenty-four hours. The OD of the samples was measured at 600 nm using a Thermo Scientific Spectronic 2000 Visible Spectrophotometer (Waltham, MA). Negative controls of media with no bacteria and positive controls of TSBG with USA300 in the absence of drug were included. A normalized bacteria density was computed using Equation (1) for all test samples. Additional release samples were tested for bacterial growth inhibition until no inhibition of bacterial growth was observed. An identical assay was conducted to examine the effect of coating time on antibacterial activity over time. Coatings were formulated as described above, except that coating times were varied (five seconds, one hour, one day, or seven days).

The antibiofilm activity of PU+auranofin coatings was also examined. PU+auranofin coatings with three or ten mg/mL auranofin used in the coating process, along with polyurethane only coatings and variations of these coatings, in which vancomycin replaced auranofin, or only auranofin (3 mg/mL) was used without any polyurethane, were examined in these studies. Vancomycin-coated catheters were first dip-coated in an ethanol solution containing the drug at either three or ten mg/mL for twenty-four hours at 20° C. These catheters were then removed from the ethanol solution and allowed to dry for twenty-four hours at 20° C. The catheters were subsequently dip-coated in fifty mg/mL polyurethane in THF for twenty-four hours at 20° C., followed by a complete drying of these coatings at 20° C. Coated or uncoated catheter segments were placed in one mL USA300 bacterial suspensions at a concentration of 104 CFU/mL in TSBG at 37° C. with shaking at 110 rpm for two hours. The samples were then removed from this suspension and rinsed three times with fresh TSBG to remove any unattached bacteria. The rinsed catheter segments were placed in new sterile vials containing five mL of fresh TSBG every twelve hours. After two days, the bacterial burden on the catheters was evaluated by examining the level of bacterial bioluminescence on the catheters using an in vivo imaging system (IVIS Lumina III, PerkinElmer, Waltham, MA). Following IVIS imaging, the biofilms were disrupted by placing the catheter segments in five mL of 1× phosphate-buffered saline (PBS) and subjected to sonication at ~40 kHz for seven min (Fisher Scientific FS30) followed by vortexing for one min. The samples were serially diluted in TSBG, plated on tryptic soy agar, and the colony-forming units (CFUs) were counted.

Example 3

Examining Coating Biocompatibility In Vitro

The biocompatibility of PU+auranofin coatings and controls was evaluated by examining erythrocyte lysis, and human hepatoma cell (ATCC HB-8065 HepG2) viability upon exposure to coated catheters or catheter incubated media, respectively. Hemolysis was examined as previously described by Gwisai et al., Biomed. Mater., 12, 045010 (2017); Zhou et al., ACS Appl. Mater. Interfaces, 9, 36269-36280 (2017)) by incubating hRBCs with PU+auranofin-coated catheters (3, 10, 30, and 60 mg/mL auranofin coating concentration), polyurethane only coatings, auranofin only coatings (three mg/mL coating concentration), and uncoated catheters. Catheters were incubated with one mL of 2% (v/v) hRBCs in 24-well plates for one hour at 37° C. Negative controls containing no catheter and only hRBCs were also included. Positive controls of the 2% hRBCs suspension incubated with 0.1% v/v Triton X-100 were included. After incubation, the plates were centrifuged at 500×g for five min. A 50 µL aliquot of the supernatant from each well was transferred to a 96-well plate. Absorbance at 540 nm was quantified using a SpectraMax M2 plate reader (Molecular Devices, San Jose, CA, USA) to measure hemolysis. Normalized hemolysis was calculated using Equation (2).

$$\text{Normalized hemolysis} = \frac{\text{sample abs} - \text{negative control abs}}{\text{positive control abs} - \text{negative control abs}} \quad (2)$$

The viability of HepG2 cells exposed to PU+auranofin coating release solutions was assessed using a colorimetric assay with WST-1. HepG2 cells were maintained in DMEM supplemented with 10% FBS at 37° C. with 5% $CO_2$. PU+auranofin-coated catheters (3 mg/mL auranofin coating concentration), polyurethane only coatings, and uncoated catheters were incubated in HepG2 culture media for twenty-four hours at 37° C. HepG2 cells were seeded at a density of $3.125\times10^6$ cells/$cm^2$ in polystyrene tissue-culture treated 96-well plates (Corning, Corning, NY) and immediately incubated with 100 µL of the different catheter incubation media at 37° C. with 5% $CO_2$. Non-coating incorporated auranofin was also included at concentrations of 0.5-32 µg/mL. After 20 hours, ten µL of WST-1 was added to each well. The plates were incubated for four hours at 37° C. with 5% $CO_2$. The absorbance (abs) of each well was measured at 450 nm using a SpectraMax M2 UV-Vis microplate reader (Molecular Devices, San Jose, CA). Normalized cell viability was calculated using Equation (3).

$$\text{Normalized cell viability} = \frac{\text{sample abs} - \text{negative control abs}}{\text{positive control abs} - \text{negative control abs}} \quad (3)$$

Example 4

In Vitro Auranofin Release from Coated Catheters and Antibacterial Efficacy

PU+auranofin catheter coatings were developed to combat complications such as bacteria attachment, infection, and biofilm development that can occur with extended catheter use. Trautner & Darouiche, Am. J. Infect. Control, 32, 177-183 (2004). To the best of our knowledge, auranofin has not previously been used in device coatings. The inventors sought to determine if auranofin was released from polyurethane coatings at concentrations effective against planktonic MRSA. Initial investigations were performed with PU+auranofin-coated catheters formulated from four concentrations of auranofin coating solution (3, 10, 30, and 60 mg/mL). Unlike many other antimicrobial agents that have a measurable absorbance (Shukla & Shukla, J. Mater. Chem. B, 6, 6444-6458 (2018)), auranofin is not readily detectable via absorbance or fluorescence spectroscopy without modification. Therefore, MRSA growth inhibition in a microdilution assay was used to estimate the concentrations of auranofin present in coated catheter release solutions. In this technique, serial dilutions of the release samples are made and incubated with MRSA. The most diluted solution able to inhibit bacterial growth is considered the upper range of the minimum inhibitory concentration of the drug in the release sample. By multiplying the dilution factor used to reach this concentration with the measured minimum inhibitory concentration of the drug, a concentration of drug in the release solution can be estimated.

FIG. S1 shows normalized MRSA density over a range of concentrations for non-coating incorporated auranofin. The minimum inhibitory concentration of non-coating incorporated auranofin against USA300 was determined to be 0.063 µg/mL, consistent with previous reports by Harbut et al., Proc. Natl. Acad. Sci. U.S.A. 112, 4453-4458 (2015); Fuchs et al., Future Med. Chem., 8(2), 117-132 (2016); and Thangamani et al., Int. J. Antimicrob. Agents, 47, 195-201 (2016). The inventors observed a transition of MRSA growth to no growth between auranofin concentrations of 0.031 and 0.063 µg/mL. Using this concentration range for non-coating incorporated auranofin and assuming no change in auranofin activity caused by the coating process, the auranofin release profile from the PU+auranofin catheter coatings was determined. FIG. 1 shows the release profile of all PU+auranofin coatings tested as a range estimated by the dilution factor required to reach minimum inhibitory concentration values. Catheters with coatings formulated using three and ten mg/mL auranofin solutions exhibited effective drug release above minimum inhibitory concentration values for eight days. Raising the drug concentration in the coatings during formulation to 30 or 60 mg/mL extended auranofin release from eight days to eleven and twenty-six days, respectively. A large auranofin release was observed for all coating formulations in the first twenty-four hours, followed by a slow, extended-release. As shown in FIG. 1, for the three mg/mL auranofin coating concentration, ~90% of the total auranofin eluted by eight days was released on the first day. Interestingly, 10, 30, and 60 mg/mL PU+auranofin samples all had similar percentages of auranofin released on the first day (~65, 66, and 62% of the total auranofin released by eight, eleven, and twenty-six days, respectively). A similar burst release for the higher auranofin coating concentrations suggests that at these concentrations, the burst release of auranofin is independent of the amount of auranofin loaded on the catheters. The cumulative release of auranofin was increased from ~7 µg for a three mg/mL auranofin coating concentration to ~37 µg for a 10 mg/mL and 30 mg/mL auranofin coating concentration and 78 µg for a 60 mg/mL auranofin coating concentration. Given that the bacterial minimum inhibitory concentration is reached with the lowest auranofin formulation concentration, this formulation could be effective in inhibiting bacterial accumulation on the implant material.

The final auranofin release values do not represent the total auranofin loading in a single 10-mm catheter segment and that some auranofin may still release below minimum inhibitory concentration values, which are not readily detectable. ICP-OES, which is capable of detecting the gold atom in auranofin molecules in non-complex solvents (e.g., water rather than PBS or media), was used to evaluate auranofin release in deionized water (pH 6) at 37° C. from PU+auranofin catheters formulated using three and ten mg/mL auranofin solutions. At eight days, 95±31 µg of auranofin had released from the three mg/mL auranofin coatings, and 319±62 µg of auranofin was released from the ten mg/mL coatings. As with the media release studies quantified using bacterial microdilution methods, a more significant cumulative release was observed from the PU+auranofin coatings formulated using ten mg/mL auranofin compared to three mg/mL auranofin at eight days. However, the values quantified for water release were significantly higher than those observed in media. These differences may arise from the differences in the release environment for the two methods used. Media components may adsorb onto or absorb into the catheter coating over time and potentially form interactions with auranofin or polyurethane, slowing drug release. The water environment lacks these interactions and may enable a more significant release. The differences in pH (pH 7.4 for the media vs. six for the water) may also factor in, as has previously been observed for polyurethane materials (Chen et al., 2014).

Figure 2:
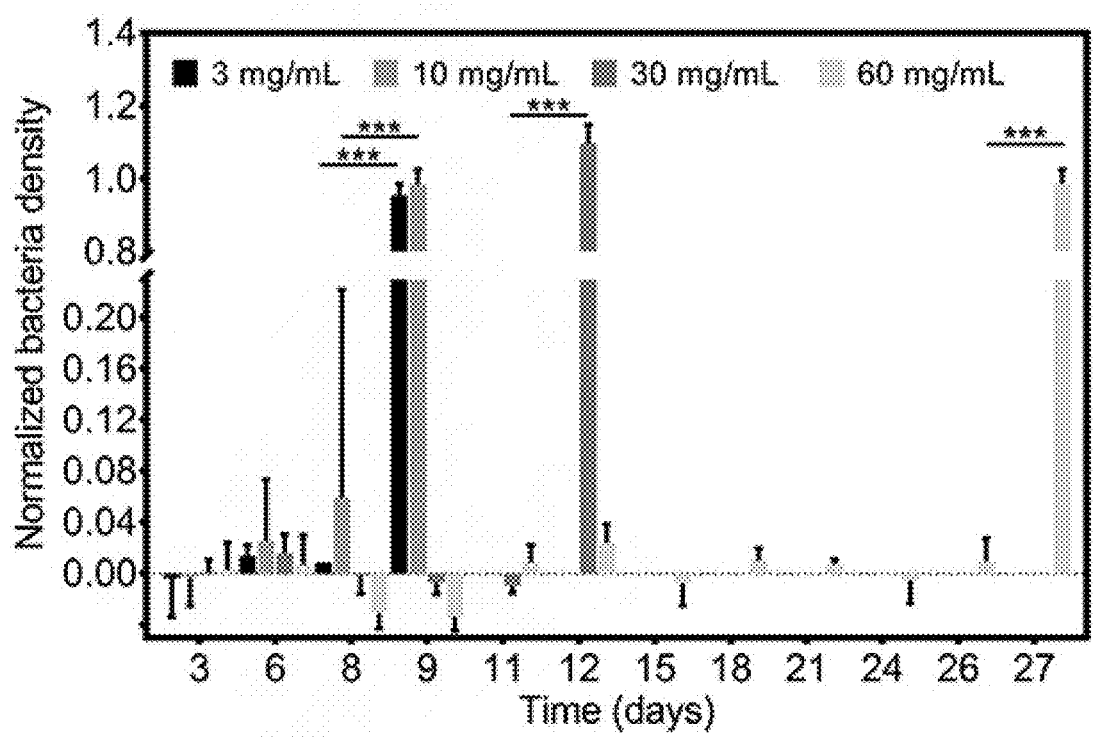
FIG. 2 is a bar graph showing the antibacterial efficacy of PU+auranofin-coated catheters. PU+auranofin coatings were formulated at four auranofin coating concentrations (3, 10, 30, and 60 mg/mL). Then, PU+auranofin-coated catheters were incubated with $2\times10^6$ CFU/mL *Staphylococcus aureus* strain MRSA USA300 bacteria. Normalized bacteria density was determined following 18 hours. The data are shown as mean±standard deviation where ***$p<0.001$ indicates significance between days using two-way ANOVA with Tukey's posthoc analysis (n=3).

The in vitro auranofin release profile studies confirmed planktonic bacterial inhibition by individual catheter release samples at PU+auranofin coating compositions formulated using 3 mg/mL, 10 mg/mL, 30 mg/mL, and 60 mg/mL auranofin. Given the potent activity of auranofin at low concentrations, the inventors examined whether auranofin release from these coatings was also able to inhibit the growth of MRSA at a 20× higher bacterial concentration than the standard microdilution assay. FIG. 2 shows the efficacy of MRSA growth inhibition for this more significant bacterial challenge ($2×10^6$ CFU/mL) upon bacterial incubation with PU+auranofin coating release solutions collected over time. The inventors found that the coating release samples were able to completely inhibit bacterial growth for samples collected at time points identical to the microdilution assays conducted at lower bacteria concentrations. PU+auranofin coatings formulated with the three and ten mg/mL auranofin were effective over eight days. In comparison, those formulated with 30 and 60 mg/mL auranofin were effective for eleven and twenty-six days, respectively. See, FIG. 2.

Having confirmed multi-day in vitro efficacy of all coating formulations examined, the inventors investigated whether changing the coating formulation process could affect effectiveness. Specifically, the inventors determined whether the catheter coating time in the PU+auranofin solution changed its efficacy. Holding the auranofin concentration in the coating solution constant at three mg/mL, the inventors examined coating times of five seconds, one hour, and seven days in addition to the one day coating time used for all other experiments. Release samples taken over time from each of these coatings were examined for their bacterial growth inhibition efficacy using a 2×10⁶ CFU/mL MRSA concentration, as shown in FIG. 3. The inventors observed that catheters coated for one and seven days behaved similarly, inhibiting MRSA growth over eight days. Interestingly, catheters coated for five seconds and for one hour exhibited antibacterial activity against MRSA for seven days. These findings show that even short coating periods lead to significant drug incorporation on the catheter capable of releasing and inhibiting bacterial growth for one week. Effective above minimum inhibitory concentration release can be extended by one day if the coating duration is increased. For the translation of these materials to the bedside, rapid production is possible without significantly compromising efficacy.

Figure 4:
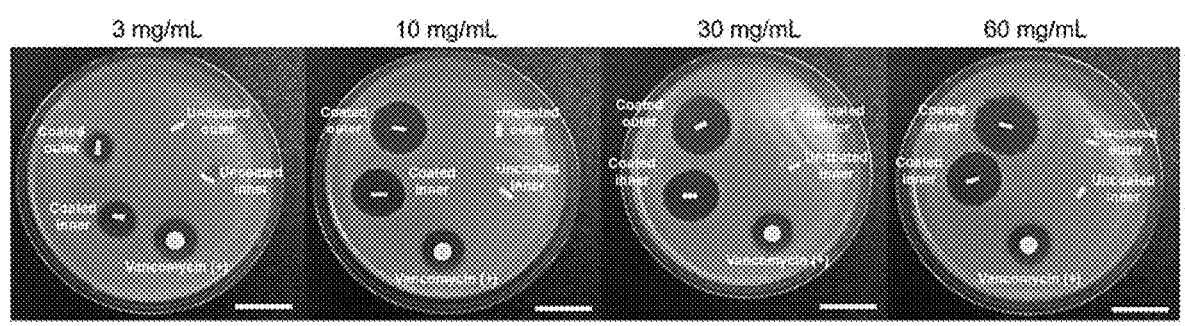
FIG. 4 is a set of photographs showing the effect of PU+auranofin catheter inner and outer surfaces on *Staphylococcus aureus* strain MRSA USA300 bacteria. Tryptic soy broth agar coated with MRSA USA300 bacteria was exposed to the inner and outer surfaces of coated bisected catheters for polyurethane only and PU+auranofin-coated materials formulated at four auranofin concentrations (3 mg/mL, 10 mg/mL, 30 mg/mL, and 60 mg/mL). Vancomycin discs containing 30 μg of vancomycin were used as positive controls Scale bar=10-mm.

Next, the inventors examined whether PU+auranofin-coated catheters were able to inhibit bacterial growth using both the inner and outer surface of the coated catheters. The results of a Kirby Bauer assay using PU+auranofin-coated catheters formulated using 3, 10, 30, and 60 mg/mL auranofin are shown in FIG. 4. For these assays, coated catheters were cut in half lengthwise and plated with either the inner surface of the catheter (i.e., the catheter lumen) or the outer surface face down on MRSA-coated agar; controls of uncoated catheters were also included. A clear zone of inhibition surrounded all PU+auranofin-coated catheter samples regardless of whether the inner or outer surface was exposed to the bacteria. In contrast, the uncoated samples did not exhibit any bacterial growth inhibition. Positive controls of 30 µg vancomycin discs were included and performed as expected, with an average zone of inhibition diameter of 1.48±0.2 cm. Quantitative comparison between inner and outer surface catheter coatings in terms of drug loading and efficacy is difficult to make as small differences in sample size and shape can alter the shape and size of the zone of inhibition that is observed surrounding these samples. Further, a degree of dose-dependent release was shown by the smaller clearing generated in the presence of the catheter material coated with three mg/mL auranofin compared to the other coating formulations examined.

The investigations demonstrated that catheter coatings generated with three and ten mg/mL auranofin were highly effective in inhibiting bacterial growth, albeit over shorter timescales compared to the 30 and 60 mg/mL auranofin coating conditions. For in vitro characterization, the inventors proceeded with using the three and ten mg/mL auranofin coating concentrations for further analysis of coating morphology, mechanical properties, antibiofilm efficacy, and cytocompatibility. For conditions that may require a lengthier application, the higher auranofin coating concentrations of 30 and 60 mg/mL are useful embodiments.

Example 5

In Vitro Antibiofilm Efficacy of Coated Catheters

The inventors next determined how biofilm formation was affected by the drug coatings. Auranofin was previously suggested to inhibit preformed *Staphylococcus aureus* biofilms within two hours of exposure, although with limited bactericidal activity likely due to the lack of metabolic activity required for target effectiveness within biofilm bacteria. Torres et al., Antimicrob. Agents Chemother., 60(10), 5663-5672 (2016).

Figure 7A:
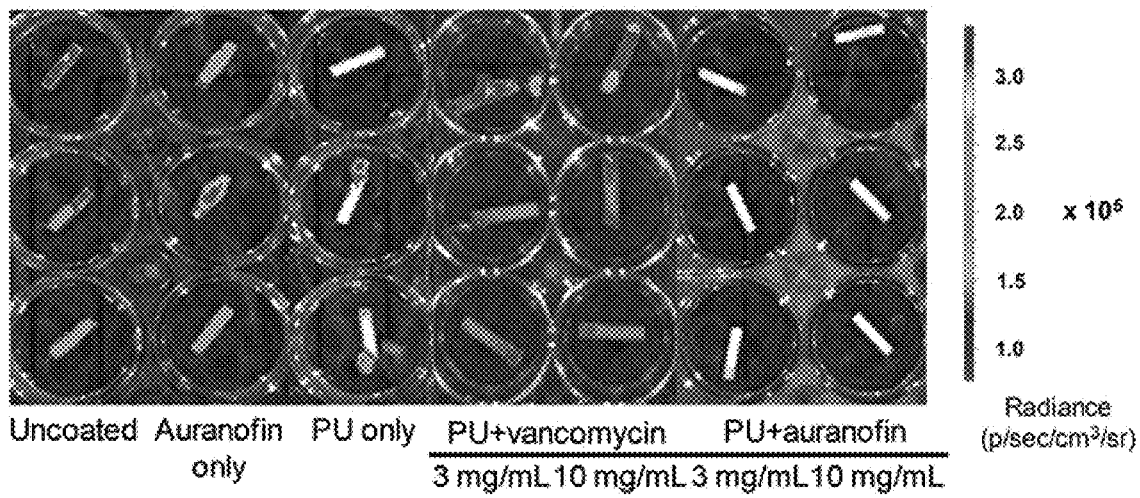
FIG. 7(A) is a photograph showing the bioluminescence (radiance) of *Staphylococcus aureus* strain MRSA USA300 Lac::Lux. The image was taken using a Perkin Elmer In Vivo Imaging System (IVIS) with the colors representing different levels of bacteria bioluminescence. Catheters were either uncoated or coated with auranofin only (at a three mg/mL coating concentration), polyurethane only, PU+vancomycin, or PU+auranofin at two drug coating concentrations (three and ten mg/mL). Samples were exposed to MRSA USA300, rinsed, and potentially attached biofilms were allowed to mature over two days before measurement.
Figure 7B:
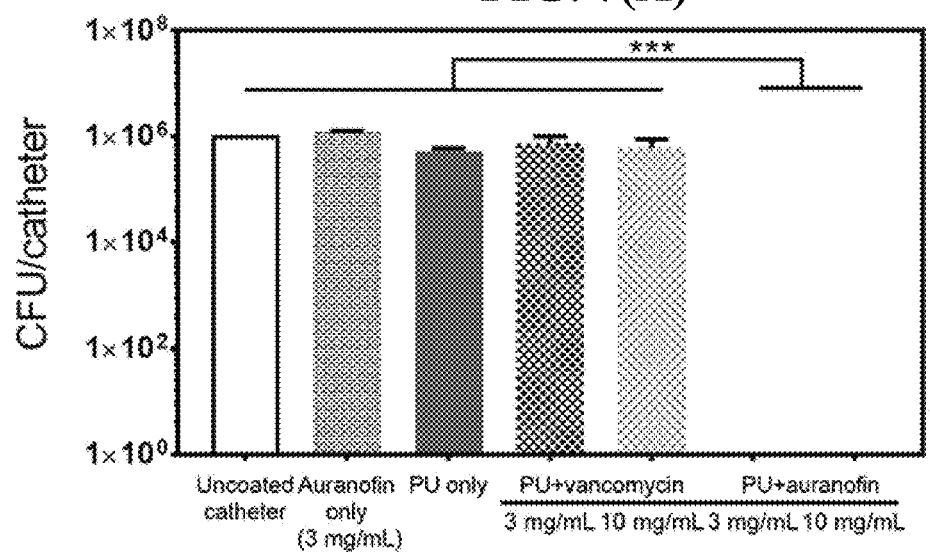
FIG. 7(B) is a bar graph showing the colony-forming units (CFU) of USA300 bacteria recovered from the different catheter groups imaged in FIG. 7(A). The data are shown as mean±standard deviation where ***$p<0.001$ indicates significance between CFU for the samples evaluated using one-way ANOVA (n=3). The PU+auranofin coated catheters on the right show no signs of bacteria build-up in bioluminescence imaging, whereas uncoated catheters or catheters coated with traditional antibiotics show signs of bacterial colonization.

To further examine the potential for using PU+auranofin-coated catheters clinically, coated catheter segments formulated using three and ten mg/mL auranofin were exposed to MRSA and then examined for biofilm formation over 48 hours. PU+vancomycin, auranofin only (lacking polyurethane, formulated with three mg/mL auranofin), and polyurethane only coatings were also examined along with uncoated catheters. Vancomycin is a potent glycopeptide antibiotic highly effective against MRSA. Abebe et al., Hosp. Med. Clin., 3, e32-e49 (2014). Vancomycin was loaded onto the catheters as a control to test its antibiofilm efficacy in comparison to auranofin coatings. Biofilm accumulation on catheter segments was visualized using an IVIS imaging system, as seen in FIG. 7A with luminescence indicating the presence of bacteria. Subsequently, the number of colony-forming units (CFUs) attached to catheters was quantified by detaching the colonies and counting, as shown in FIG. 7B. Except for the PU+auranofin coatings, all catheters tested exhibited bacterial luminescence. Both PU+auranofin formulations completely inhibited bacterial attachment.

PU+vancomycin and auranofin only coatings did not exhibit any statistical difference in bacterial CFU attachment as compared to uncoated catheters. Due to vancomycin hydrophilicity, the inventors hypothesize that vancomycin is released rapidly from these coatings, leading to a lack of efficacy in preventing biofilm formation. Auranofin only coatings are also likely highly unstable due to the lack of a polymer carrier and are similarly unable to prevent bacterial attachment.

Polyurethane only coatings showed a 1-log reduction in the bacterial attachment as compared to uncoated catheters. This antibiofilm activity of polyurethane has previously been observed. Martinez-Martinez et al., J. Hosp. Infect. 16 311-8 (1990); Lopez-Lopez et al., J. Med. Microbiol. 34, 349-353 (1991); Zdrahala & Zdrahala, 1999). This antibiofilm activity of polyurethane may occur due to the smooth polyurethane surface, which the inventors observed using scanning electron microscopy. Overall, formulating auranofin in a polyurethane catheter coating enabled both bacterial growth inhibition in planktonic cultures over time and complete prevention of bacterial surface attachment, unlike either polyurethane or auranofin alone.

Example 6

In Vitro Cytotoxicity Evaluation of Coated Catheters

Figure 8A:
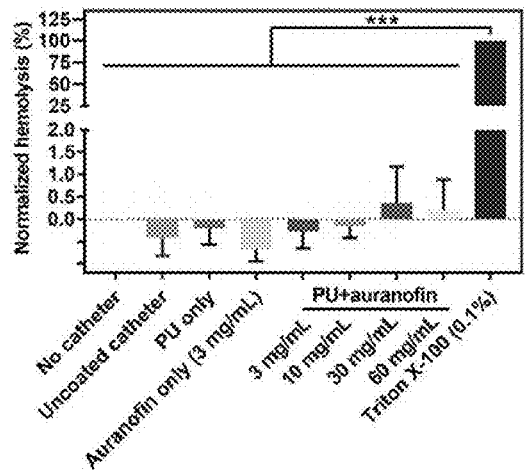
FIG. 8(A) shows the percent normalized hemolysis of hRBCs exposed to uncoated catheters, polyurethane only, auranofin only (formulated at a three mg/mL auranofin coating concentration). PU+auranofin (formulated at 3 mg/mL, 10 mg/mL, 30 mg/mL, and 60 mg/mL auranofin coating concentrations) compared to negative controls of untreated hRBCs and a Triton X-100 incubated positive control.

The PU+auranofin coatings of the invention are useful as antibacterial materials. Future translation of these materials requires that the materials are biocompatible. The drug-coated catheters will eventually be used as functioning devices. They will be exposed to circulating blood. For this reason, the inventors tested the auranofin-coated devices in the presence of human erythrocytes to see if the various drug coating concentrations incite lysis. The hemolysis of PU+auranofin coatings at all formulations developed (i.e., 3, 10, 30, and 60 mg/mL of auranofin coating concentrations), polyurethane only coatings, auranofin only coatings (formulated using a three mg/mL auranofin solution), and uncoated catheters were compared with hRBC negative and positive controls (i.e., untreated and Triton X-100 treated hRBCs, respectively), as shown in FIG. 8A. The inventors did not observe any significant difference in normalized hemolysis between any of the tested coating groups and the untreated controls, indicating excellent hemocompatibility of the PU+auranofin-coated catheters.

Figure 8B:
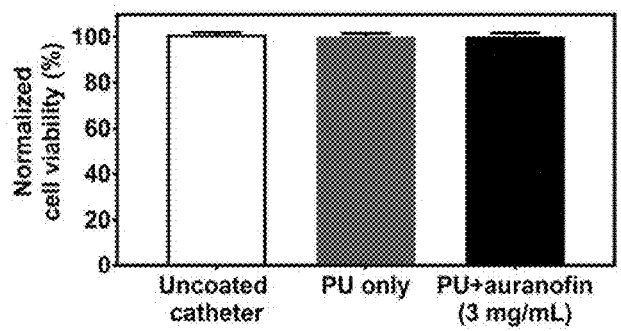
FIG. 8(B) shows the normalized HepG2 liver cell viability upon exposure to media incubated with uncoated catheters, polyurethane only, and PU+auranofin (formulated at a three mg/mL auranofin coating concentration) catheters for twenty-four hours. Data are shown as mean±standard deviation. Statistical significance was evaluated using one-way ANOVA (n=3) and is displayed as ***p<0.001, indicating statistical significance between the positive control (Triton X-100 with hRBCs) and other conditions tested. No statistical significance was noted between the other hemolysis conditions tested or between the different HepG2 viability conditions examined (p>0.5).
Figure 9:
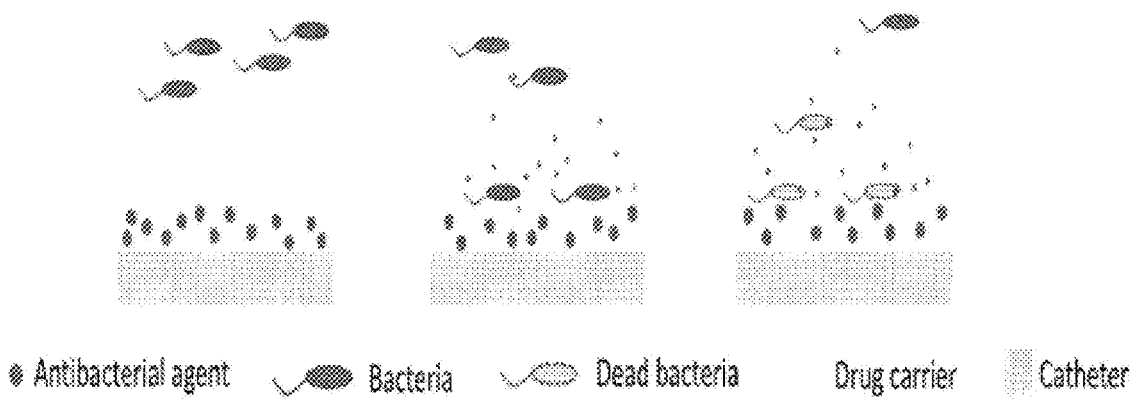
FIG. 9 shows the design of an intravascular catheter coating with long-term antibacterial and antibiofilm efficacy.
Figure 10:
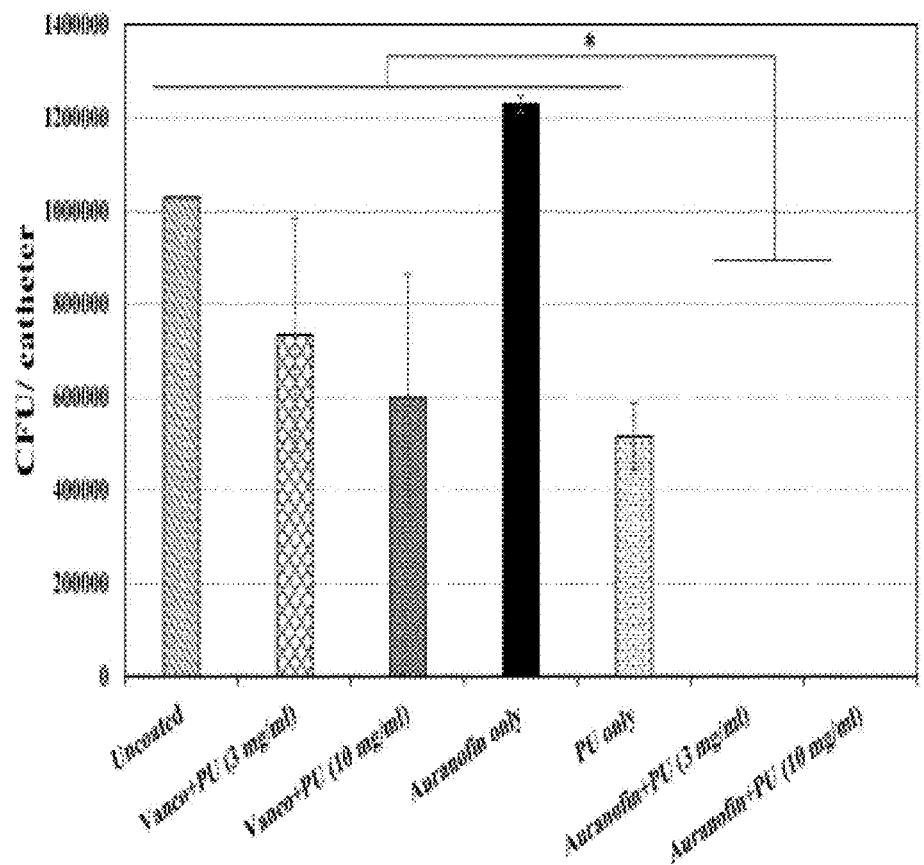
FIG. 10 is a bar graph showing that PU+auranofin-coated catheters are better at inhibiting bacterial growth than other catheter treatments.
Figure 11:
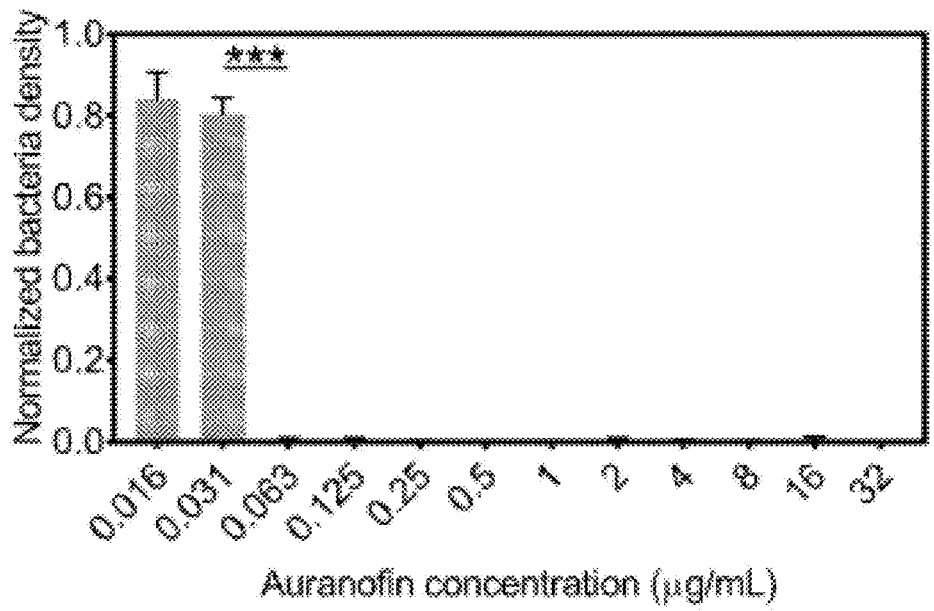
FIG. 11 is a bar graph showing the minimum inhibitory concentration (MIC) of auranofin against *Staphylococcus aureus* strain MRSA USA300. The data are shown as mean±standard deviation where *** p<0.001 between auranofin concentrations evaluated using one-way ANOVA (n=3).
Figure 12:
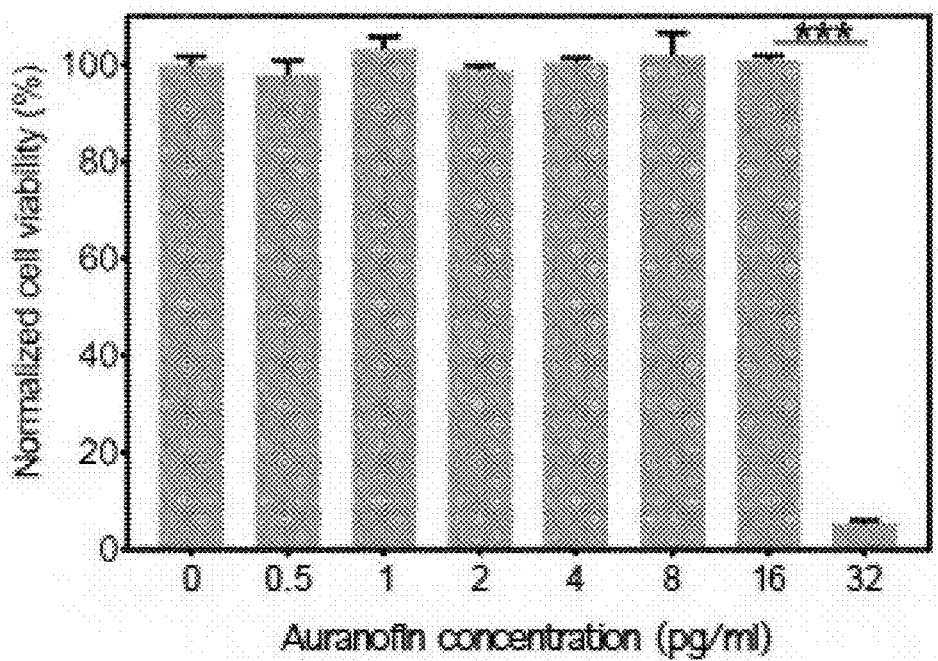
FIG. 12 is a bar graph showing auranofin toxicity to liver hepatocellular carcinoma (HepG2) cells. The data are shown as mean±standard deviation where ***p<0.001 between auranofin concentrations evaluated using one-way ANOVA (n=3).

The inventors evaluated the cytotoxicity of PU+auranofin coatings formulated using three mg/mL auranofin, polyurethane only, and uncoated catheters incubated in cell culture media for twenty-four hours on hepatocellular carcinoma cells. HepG2 cells were selected due to their widespread use as in vitro models for liver metabolism of toxins. Guillouzo et al., Chem. Biol. Interact., 168, 66-73 (2007). Initially, the inventors examined the viability of HepG2 cells with non-coating incorporated auranofin (FIG. S2). The inventors observed that the half-maximal inhibitory concentration ($IC_{50}$) for viability for non-coating incorporated auranofin fell between 16 and 32 µg/mL, which corresponds with IC50 values of auranofin previously reported for HepG2 cells. Liu et al., Oncoscience, 2, 457-466 (2015). FIG. 8B shows the percentage of viable cells upon exposure to catheter release media. None of the formulations tested affected the viability of HepG2 cells compared to the no catheter control. From the in vitro media release studies, a concentration of three µg/mL auranofin for the twenty-four hours release sample could be estimated, falling well below the $IC_{50}$ concentration. The catheter alone and polyurethane alone coating was not expected to have any effect on the cells, as previously FDA approved materials.

Similarly, auranofin is typically administrated orally to patients at an auranofin concentration of six mg/mL per day for antirheumatic therapy. It has demonstrated no cumulative toxicity during long-term treatments. Egsmose et al., J. Rheumatol., 22, 2208-2213 (1995). Therefore, auranofin has terrific potential to be used as an antibacterial and antibiofilm therapy without significant concern for human toxicity.

LIST OF EMBODIMENTS

Specific compositions and methods of auranofin-releasing antibacterial and antibiofilm polyurethane intravascular coatings have been described. The detailed description in this specification is illustrative and not restrictive. The detailed description in this specification is not intended to be exhaustive or to limit the disclosure to the precise form disclosed. Other equivalents and modifications besides those already described are possible without departing from the inventive concepts described in this specification, as those skilled in the art will recognize. While method steps or functions are presented in a given order, alternative embodiments may perform functions in a different order, or functions may be performed substantially concurrently. Due to biological functional equivalency considerations, some changes can be made in a protein structure without affecting the biological or chemical action in kind or amount. The inventive subject matter, therefore, is not to be restricted except in the spirit of the disclosure.

When interpreting the disclosure, all terms should be interpreted in the broadest possible manner consistent with the context. Unless otherwise defined, all technical and scientific terms used in this specification have the same meaning as commonly understood by one of ordinary skill in the art to which this invention belongs. This invention is not limited to the particular methodology, protocols, reagents, and the like described in this specification and, as such, can vary in practice. The terminology used in this specification is not intended to limit the scope of the invention, which is defined solely by the claims.

All patents and publications cited throughout this specification are expressly incorporated by reference to disclose and describe the materials and methods described in such publications that might be used in connection with the technologies described in this specification. The publications discussed herein are provided solely for their disclosure before the filing date. In this regard should be construed as an admission that the inventors are not entitled to antedate such disclosure by prior invention or for any other reason. If there is an apparent discrepancy between a prior patent or publication and the description provided in this specification, the present specification (including any definitions) and claims shall control. All statements as to the date or representation as to the contents of these documents are based on the information available to the applicants and do not constitute any admission as to the correctness of the dates or contents of these documents. The dates of publication provided in this specification may be different from the actual publication dates. If there is an apparent discrepancy between a publication date provided in this specification and the actual publication date supplied by the publisher, the actual publication date shall control.

The terms "comprises" and "comprising" should be interpreted as referring to elements, components, or steps in a non-exclusive manner, indicating that the referenced elements, components, or steps may be present, used, or combined with other elements, components, or steps. The singular terms "a," "an," and "the" include plural referents unless context indicates otherwise. Similarly, the word "or" is intended to cover "and" unless the context indicates otherwise. The abbreviation "e.g." is used to indicate a non-limiting example and is synonymous with the term "for example."

When a range of values is provided, each intervening value, to the tenth of the unit of the lower limit, unless the context dictates otherwise, between the upper and lower limit of that range and any other stated or intervening value in that range of values.

Some embodiments of the technology described herein can be defined according to any of the following paragraphs:

An antibacterial coating, comprising: (a) auranofin; and (b) polyurethane.

The antibacterial coating, wherein the coating covers a catheter, glass, or poly(tetrafluoroethylene).

The antibacterial coating, wherein the coating prevents catheter-related bloodstream infections.

The antibacterial coating, wherein the coating prevents biofilms from forming around catheters inserted into a vertebral body.

The antibacterial coating, wherein the coating is hemocompatible.

A device, covered by an antibacterial coating comprising: (a) auranofin; and (b) polyurethane.

The device, wherein the device is a catheter.

A method of making a device comprising an antibacterial coating comprising the step of dip-coating the device in an antibacterial coating comprising (a) auranofin; and (b) polyurethane.

A method of preventing a catheter-related bloodstream infection, comprising the step of inserting a polyurethane+auranofin-coated catheter into the body of a vertebrate.

The method, wherein the catheter-related bloodstream infection is caused by methicillin-resistant *Staphylococcus aureus* (MRSA).

The method, wherein the catheter-related bloodstream infection is a biofilm.

The method, wherein the antibacterial coating can stretch up to 500% without breaking.

A method of treating a catheter-related bloodstream infection, comprising the step of inserting a polyurethane+auranofin-coated catheter into the body of a vertebrate, wherein the has a catheter-related bloodstream infection.

The method, wherein the treatment is continued for at least eight days.

The method, wherein the treatment is continued for at least twenty-six days.

We claim:

1. An antibacterial coating covering a catheter, glass, or poly(tetrafluoroethylene), wherein:
   (a) the antibacterial coating consists of a dried, homogenous solution of auranofin dissolved in polyurethane; and
   (b) wherein a portion of the auranofin is hydrogen bonded with the polyurethane;
      wherein the antibacterial coating is operative to provide a larger burst rate of release of auranofin into an aqueous environment in the first 24 hours of contact with said environment, followed by a slower and extended rate of release after the first 24 hours;
      wherein the antibacterial coating is operative to stretch up to about 500% elongation without breaking; and
      wherein the antibacterial coating with the homogenously dissolved auranofin is made to cover the catheter, glass, or poly(tetrafluoroethylene by a dip-coating process including the steps of dipping the catheter, glass, or poly(tetrafluoroethylene) in a homogeneous polyurethane-auranofin-solvent solution and evaporating the solvent, to deposit the antibacterial coating consisting of a dried, homogeneous solution of auranofin dissolved in polyurethane.

2. The antibacterial coating of claim 1, wherein the coating prevents catheter-related bloodstream infections.

3. The antibacterial coating of claim 1,
   wherein the catheter has been inserted into a vertebral body; and
   wherein the antibacterial coating prevents biofilms from forming around the catheter inserted into the vertebral body.

4. The antibacterial coating of claim 1, wherein the coating is hemocompatible.

5. The antibacterial coating of claim 1, wherein the auranofin is released in vivo for at least 25 days.

6. The antibacterial coating of claim 1, wherein the auranofin provides anti-biofilm activity against methicillin-resistant *Staphylococcus aureus* for at least 25 days.

7. The antibacterial coating of claim 1, wherein the dip-coating process is for at least twenty-four hours.

8. A device, covered by an antibacterial coating wherein:
   (a) the antibacterial coating consists of a dried, homogenous solution of auranofin dissolved in polyurethane; and
   (b) wherein a portion of the auranofin is hydrogen bonded with the polyurethane;
      wherein the antibacterial coating is operative to provide a larger burst rate of release of auranofin into an aqueous environment in the first 24 hours of contact with said environment, followed by a slower and extended rate of release after the first 24 hours;
      wherein the antibacterial coating is operative to stretch up to about 500% elongation without breaking; and
      wherein the antibacterial coating with the homogenously dissolved auranofin is made to cover the device by a dip-coating process including the steps of dipping the device in a homogeneous polyurethane-auranofin-solvent solution and evaporating the solvent, to deposit the antibacterial coating consisting of a dried, homogenous solution of auranofin dissolved in polyurethane.

9. The device of claim 8, wherein the device is a catheter.

10. The device of claim 8, wherein the auranofin is released in vivo for at least 25 days.

11. The device of claim 8, wherein the auranofin provides anti-biofilm activity against methicillin-resistant *Staphylococcus aureus* for at least 25 days.

12. The device of claim 8, wherein the dip-coating process is for at least twenty-four hours.

13. A method of making a device comprising an antibacterial coating, the method comprising the steps of:
   dipping the device in a homogeneous polyurethane-auranofin-solvent solution and evaporating the solvent, to deposit the antibacterial coating consisting of a dried, homogenous solution of auranofin dissolved in polyurethane;
   wherein a portion of the auranofin is hydrogen bonded with the polyurethane;
      wherein the antibacterial coating is operative to provide a larger burst rate of release of auranofin into an aqueous environment in the first 24 hours of contact with said environment, followed by a slower and extended rate of release after the first 24 hours; and
      wherein the antibacterial coating is operative to stretch up to about 500% elongation without breaking.

14. The method of claim 13, wherein the auranofin is released in vivo for at least 25 days.

15. The method of claim 13, wherein the auranofin provides anti-biofilm activity against methicillin-resistant *Staphylococcus aureus* for at least 25 days.

16. The method of claim 13, wherein the dip-coating process is for at least twenty-four hours.

17. A method of preventing a catheter-related bloodstream infection, comprising the step of:
   inserting a coated catheter including an antibacterial coating consisting of a dried homogenous solution of auranofin dissolved in polyurethane, wherein a portion of the auranofin is hydrogen bonded with the polyurethane, into the body of a vertebrate;
      wherein the antibacterial coating is operative to provide a larger burst rate of release of auranofin into an aqueous environment in the first 24 hours of contact with said environment, followed by a slower and extended rate of release after the first 24 hours;
      wherein the antibacterial coating is operative to stretch up to about 500% elongation without breaking; and
      wherein the antibacterial coating with the homogenously dissolved auranofin is made to cover the catheter by a dip-coating process including the steps of dipping the catheter, glass, or poly(tetrafluoroethylene) in a homogeneous polyurethane-auranofin-solvent solution and evaporating the solvent, to deposit the antibacterial coating consisting of a dried, homogeneous solution of auranofin dissolved in polyurethane.

18. The method of claim 17, wherein the catheter-related bloodstream infection is caused by methicillin-resistant *Staphylococcus aureus* (MRSA).

19. The method of claim 17, wherein the catheter-related bloodstream infection is a biofilm.

20. A method of treating a catheter-related bloodstream infection, the method comprising the steps of:
   inserting a coated catheter including an antibacterial coating consisting of a dried homogeneous solution of auranofin dissolved in polyurethane, wherein a portion of the auranofin is hydrogen bonded with the polyurethane, into the body of a vertebrate, wherein the vertebrate has a catheter-related bloodstream infection;
      wherein the antibacterial coating is operative to provide a larger burst rate of release of auranofin into an aqueous environment in the first 24 hours of contact with said environment, followed by a slower and extended rate of release after the first 24 hours;

wherein the antibacterial coating is operative to stretch up to about 500% elongation without breaking; and wherein the antibacterial coating with the homogenously dissolved auranofin is made to cover the catheter by a dip-coating process including the steps of dipping the catheter, glass, or poly(tetrafluoroethylene) in a homogeneous polyurethane-auranofin-solvent solution and evaporating the solvent, to deposit the antibacterial coating consisting of a dried, homogeneous solution of auranofin dissolved in polyurethane.

* * * * *